United States Patent [19]

Motomichi et al.

[11] Patent Number: 5,103,018

[45] Date of Patent: Apr. 7, 1992

[54] MITOMYCIN DERIVATIVES

[75] Inventors: Kono Motomichi; Saito Yutaka; Kanda Yutaka, all of Tokyo; Kasai Masaji, Kanagawa; Sato Akira, Tokyo; Morimoto Makoto; Ashizawa Tadashi, both of Shizuoka, all of Japan

[73] Assignee: Kyowa Hakko Kogyo Kabushiki Kaisha, Japan

[21] Appl. No.: 204,429

[22] PCT Filed: Aug. 28, 1987

[86] PCT No.: PCT/JP87/00640

§ 371 Date: Oct. 31, 1988

§ 102(e) Date: Oct. 31, 1988

[87] PCT Pub. No.: WO88/01622

PCT Pub. Date: Mar. 10, 1988

[30] Foreign Application Priority Data

Aug. 26, 1986 [JP] Japan .................. 61-203230

[51] Int. Cl.$^5$ .................. C07D 487/04; A61K 31/40
[52] U.S. Cl. .................. 548/422
[58] Field of Search .................. 548/422; 514/410

[56] References Cited

U.S. PATENT DOCUMENTS 4,927,943  5/1990  Vyas et al. .................. 548/422

Primary Examiner—Nicholas S. Rizzo
Attorney, Agent, or Firm—Schweitzer Cornman & Gross

[57] ABSTRACT

Mitomycin derivatives containing substituted dithioethylamino groups at the 7th position are provided. The mitomycin derivatives according to the present invention are superior to mitomycin C with respect to their improved anti-tumour activity and toxicity. More particularly, they exhibit a wider tolerance of dosage against Sarcoma 180A solid tumour as well as a better survival time and weaker bone marrow supression against P388.

Furthermore, certain compounds exhibit a high water-solubility which is advantageous for pharmaceutical purposes. Excellent anti-tumour agents may readily be prepared by using the derivatives of the present invention.

1 Claim, No Drawings

MITOMYCIN DERIVATIVES

TECHNICAL FIELD

The present invention relates to mitomycin derivatives having anti-tumour activity and pharmaceutical compositions containing the same.

BACKGROUND ART

Mitomycins have excellent anti-tumour activity, whilst they are liable to exhibit certain undesired side effects such as the decrease of leucocytes. Thus, attempts have been made to provide various mitomycin derivatives to increase anti-tumour activity and/or to decrease toxicity.

The known mitomycin derivatives include mitomycin C derivatives and porfiromycin derivatives, which contain a substituted 7-amino group, disclosed, for example, in U.S. Pat. No. 4,268,676; Japanese laid open Patent Applications 92288/81 and 188590/82; Journal of Medicinal Chemistry, 24, 975–981 (1981); ibid., 26, 16–20 (1983) and ibid., 26, 1453–1457 (1983)]. These prior art literatures disclose that mitomycin derivatives containing a substituted amino group at the 7th position exhibit anti-tumour activity in the living body.

Among various mitomycin derivatives containing a substituted 7-amino group, those having a 7-amino group substituted with a sulphur atom are exemplified by the mitomycin derivatives containing at the 7th position 2-thiazolamino group, 2-thienylmethylamino group and (4-sulfonamidophenyl)methylamino group (disclosed in Japanese laid open Patent Application 92288/81), 2-mercaptoethylamino group, 2-ethylthioethylamino group, thiomorpholino group, thiazolidinyl group, 4-mercaptoanilino group, 2-(4-methylthiazolyl-)amino group, 2-(5-methyl-1,3,4-thiadiazolyl)amino group and 4-(2,1,3-benzothiadiazolyl)amino group (disclosed in Japanese laid open Patent Application 188590/82).

Examples of the known mitomycin derivatives containing at the 7th position a substituent of the formula:

RSS(CH$_2$)$_2$NH—, include those, of which R is an an alkyl or substituted alkyl such as 7-N-propyldithioethylmitomycin C, 7-N-methoxycarbonylmethyldithioethylmitomycin C and 7-N-[2-(2-hydroxyethyldithio)ethyl]mitomycin C (disclosed, for example, in EP0116208A1 and Japanese laid open Patent Application 175493/84). Those, of which R contains an aromatic ring having a substituent, are exemplified by 7-N-[2-(4-acetamidophenyldithio)ethyl]-mitomycin C (disclosed in EP 0116208A1 and Japanese laid open Patent Application 175493/84) and 7-N-[2-(4-fluorophenyldithio)ethyl]mitomycin C (disclosed in EP 0163550A2 and Japanese laid open Patent Application 255789/75). Those, of which R contains a structural component of an amino acid having a thiol group or a peptide having the foregoing amino acid are exemplified by 7-N-[2-[(L-cystein-S-yl)thio]ethyl]mitomycin D and 7-N-[2-[(glycino-L-cystein-S-yl)thio]ethyl]mitomycin C, etc. (disclosed in EP0163550A2 and Japanese laid open Patent Application 255789/85 etc.)

Mitomycin derivatives containing at the 7th position a substituent of the formula:

—NHCH$_2$CH$_2$SSCH$_2$CH$_2$NH—, are exemplified by 7-N, 7'-N'-dithiodiethylenedimitomycin C, 7-N, 7'-N'-dithiodiethylenedimitomycin D, 7-N-[2-(2-aminoethyl)dithioethyl]mitomycin C, 7-N-[2-(2-aminoethyl)dithioethyl]mitomycin D (disclosed in EP 0116208A1, Japanese laid open Patent Applications 104386/84 and 175493/84) etc.

Derivatives of mitomycin C containing

R$^8$—SS—alk$_2$—NH at the 7th position, are exemplified by the known compounds containing at the 7th position $$\underset{\text{O}}{\overset{\parallel}{\text{RCNHCH}_2\text{CH}_2\text{SSCH}_2\text{CH}_2\text{NH}}},$$

in which R is exemplified by

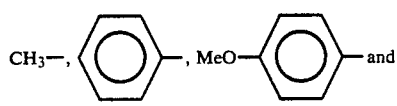

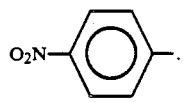

(disclosed in Japanese laid open Patent Application 205382/84). However, in the executional examples, only the derivatives of mitomycin C and 1a-acetylmitomycin C, both containing at the 7th position $$\underset{\text{O}}{\overset{\parallel}{\text{CH}_3\text{CNHCH}_2\text{CH}_2\text{SSCH}_2\text{CH}_2\text{NH}}}$$

are disclosed, and other compounds and their physico-chemical characteristics and anti-tumour effects are not disclosed.

An object of the present invention is to provide mitomycin derivatives containing a substituted amino group at the 7th position having higher anti-tumour activity, lower side effects and/or higher solubility which is desirable in pharmaceutical preparation and anti-tumour compositions containing the same.

DISCLOSURE OF THE INVENTION

The present invention provides mitomycin derivatives represented by the following formula (I):

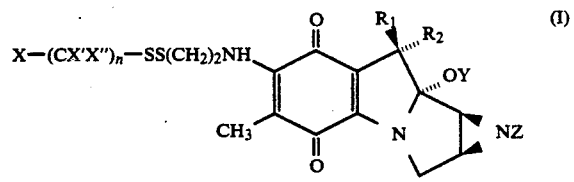

wherein
X' and X" each independently represents hydrogen or lower alkyl;
Y and Z each independently represents hydrogen or methyl; provided that when Z is hydrogen, Y is methyl;
one of R$_1$ and R$_2$ represents carbamoyloxymethyl and the other represents hydrogen;

n represents an integer of from 1 to 4;
and X is selected from the following (1) to (4):

$$R_3NH, R_3O \text{ or } R_3S \quad (1)$$

wherein $R_3$ is selected from the residue of an organic acid, from which OH of the carboxyl group has been removed, lower alkanoyl and halogen-substituted lower alkanoyl; said organic acid is selected from α-amino acids, orotic acid, isoorotic acid, nicotinic acid, isonicotinic acid, thiophenecarboxylic acid, furancarboxylic acid, vitamin A acid, fatty acid-saturated mono- and dicarboxylic acids and fatty acid-unsaturated mono- and dicarboxylic acids;

provided that when said α-amino acid contains a second carboxyl group, the second carboxyl group may be protected by lower alkyl or may form a salt with an alkali metal, ammonium or organic amine;

optionally the amino group of said α-amino acid may be protected by lower alkanoyl or may form a salt with an inorganic or organic acid; provided that when said dicarboxylic acid contains a second carboxyl group, said second carboxyl group may be protected by a lower alkyl or may form an ester-coupling with a phenolic hydroxy group of tocopherol or may form a salt with an alkali metal, ammonium or organic amine; and provided that when $R_1$ represents a carbamoyloxymethyl and $R_2$ represents a hydrogen atom, $R_3$ of $R_3NH$ does not represent a lower alkanoyl;

(2)

wherein $R_4$ is selected from the residue of an alcohol or organic amine, from which H has been removed; said alcohol is selected from β-estradiol, β-estradiol 3-benzoate, retinol, cortisone and corticosterone; said organic amine is selected from ammonia, primary amines, secondary amines, α-amino acids, isoproterenol, epinephrine and norepinephrine;

provided that when said α-amino acid contains a second amino group, the second amino group may be protected by lower alkanoyl or may form a salt with an organic acid or inorganic acid;

optionally the carboxyl group of said α-amino acid may be protected by lower alkyl or may form a salt with an alkali metal, ammonium or organic amine;

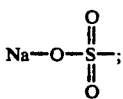
(3)

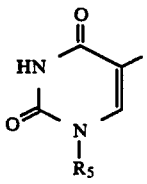
(4)

wherein $R_5$ is hydrogen, ribofuranosyl or 2-deoxyribofuranosyl; and $(CX'X'')_n$ is $CH_2$.

In this specification, compounds represented by the formula (I) are designated as Compounds I. Compounds of other formulae are also designated similarly.

With regard to the definition of Compounds I, lower alkyl are exemplified by alkyl having 1–4 carbon atoms such as, for example, methyl, ethyl, n-propyl and t-butyl.

Examples of suitable α-amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, of which absolute configuration may be in L, D or DL form.

Suitable fatty acid-saturated monocarboxylic acids are exemplified by tetradecanoic acid, hexadecanoic acid, and octadecanoic acid. Suitable fatty acid-saturated dicarboxylic acids are exemplified by malonic acid, succinic acid and glutaric acid.

Suitable fatty acid-unsaturated monocarboxylic acids include, for example, oleic acid and linoleic acid. Suitable fatty acid-unsaturated dicarboxylic acids are exemplified by maleic acid and fumaric acid.

Examples of suitable lower alkanoyl include alkanoyl groups having 1–4 carbon atoms such as, for example, formyl, acetyl, propanoyl, n-butanoyl and t-butanoyl.

Suitable halogen-substituted lower alkanoyl include, for example, chloroacetyl, dichloroacetyl, trichloroacetyl, fluoroacetyl, difluoroacetyl, trifluoroacetyl, 2-chloropropionyl, 3-chloropropionyl and 2,3-dichloropropionyl.

Suitable primary amines are exemplified by ethylamine and monoethanolamine. Suitable secondary amines include, for example, pyrrolidine, piperidine, morpholine and thiomorpholine.

Suitable alkali metals are exemplified by sodium and potassium.

Suitable organic amines which may be used to form salts include, for example, monoethanolamine, N-methylglucamine and triethanolamine.

Suitable inorganic acids which may be used to form salts include, for example, carbonic acid, sodium bisulfate, potassium dihydrogen phosphate and sodium dihydrogen phosphate.

Suitable organic acids are exemplified by ascorbic acid, citric acid, succinic acid, acetic acid, tartaric acid and lactic acid.

It has been found that, in the formula (I), wherein Z is hydrogen, it is possible by the following rearrangement (equilibrium) reaction to convert Compounds I into albomitomycin-type Compounds (I') which are also new compounds:

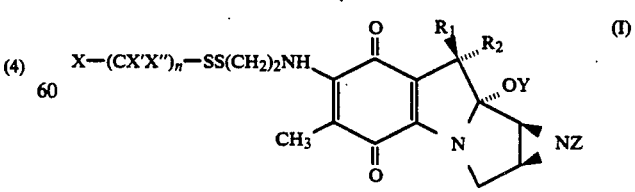
(I)

-continued

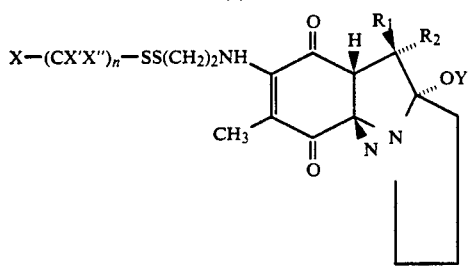

(wherein X, X', X'', $R_1$, $R_2$, Y and n are as hereinbefore defined).

The existence of albomitomycin-type and mitomycin-type mitomycin A and mitomycin C was previously known (Abstracts, the 27th Symposium on the Chemistry of Natural Products, pp. 672–679 1985, Hiroshima).

In the case wherein the compound of Example 1 described hereinafter was equilibrated by allowing to stand in an aqueous solution (5 mg/ml) at a temperature of 25° C. for 24 hours, the molar ratio of the albomitomycin-type substance was 8.5%.

It has been found that the albomitomycin-type substances of the present invention are gradually converted into mitomycin-type substances. In the case of Compound I, for example, the compound had a half-time of 50 minutes and was equilibrated with mitomycin-type substance within a period of 5 hours by treating in an aqueous solution (5 mg/ml) at a temperature of 26° C.

Thus, it is believed, on the ground of the observation of mitomycin C, that the existence of albomitomycin-type substances may not harm the anti-tumour activity of the corresponding mitomycin-type substances.

Moreover, it is possible to maintain a constant ratio between mitomycin-type substance and albomitomycin-type substance found in any compound of the present invention by selecting the reaction conditions appropriately. In summary, the existence of substances of two types in one compound of the present invention may not, in our view, give rise to deleterious effects with respect to clinical practice.

The following Tables 1 and 2 indicate the names and structures of Compounds I according to the present invention.

TABLE 1

| No. | Compound |
|---|---|
| 1 | 7-N-[2-[[2-($N^5$-L-glutamino)ethyl]dithio]ethyl]-mitomycin C |
| 2 | 7-N-[2-[[2-($N^5$-L-glutamino)ethyl]dithio]ethyl]-mitomycin D |
| 3 | 7-N-[2-[[2-($N^5$-D-glutamino)ethyl]dithio]ethyl]-mitomycin C |
| 4 | 7-N-[2-[[3-($N^5$-L-glutamino)propyl]dithio]ethyl]-mitomycin C |
| 5 | 7-N-[2-[[4-($N^5$-L-glutamino)butyl]dithio]ethyl]-mitomycin C |
| 6 | 7-N-[2-[[2-($N^4$-L-asparagino)ethyl]dithio]ethyl]-mitomycin C |
| 7 | 7-N-[2-[[2-($N^2$-L-asparagino)ethyl]dithio]ethyl]-mitomycin C |
| 8 | 7-N-[2-[[2-(L-pyroglutamylamino)ethyl]dithio]-ethyl]mitomycin C |
| 9 | 7-N-[2-[[2-($N^2$-L-glutamino)ethyl]dithio]ethyl]-mitomycin C |
| 10 | 7-N-[2-[[2-($N^4$-L-asparagino)ethyl]dithio]ethyl]-mitomycin D |
| 11 | 7-N-[2-[[2-($N^5$-D-glutamino)ethyl]dithio]ethyl]-mitomycin D |
| 12 | 7-N-[2-[[2-(L-pyroglutamylamino)ethyl]dithio]-ethyl]mitomycin D |
| 13 | 7-N-[2-[[2-(L-prolylamino)ethyl]dithio]ethyl]-mitomycin C |
| 14 | 7-N-[2-[(2-orotamidoethyl)dithio]ethyl]mitomycin C |
| 15 | 7-N-[2-[2-retinamidoethyl)dithio]ethyl]mitomycin C |
| 16 | 7-N-[2-[[2-[(2R, 4R, 8R)-2, 5, 7, 8-tetramethyl-2-(4, 8, 12-trimethyltridecyl)-2H-1-benzopyran-6-yl]-oxycarbonyl]ethyl]carboxamido]ethyl]dithio]ethyl]-mitomycin C |
| 17 | 7-N-[2-[(2-acetamidoethyl)dithio]ethyl]mitomycin D |
| 18 | 7-N-[2-[(2-formamidoethyl)dithio]ethyl]mitomycin D |
| 19 | 7-N-[2-[(2-trifluoroacetamidoethyl)dithio]ethyl]-mitomycin C |
| 20 | 7-N-[2-[(2-trifluoroacetamidoethyl)dithio]ethyl]-mitomycin D |
| 21 | 7-N-[2-[(2-carbamoylethyl)dithio]ethyl]mitomycin C |
| 22 | 7-N-[2-[[2-[[(1S)-4-amino-1-carboxybutyl]-carbamoyl]ethyl]dithio]ethyl]mitomycin C |
| 23 | 7-N-[2-[[2-[[(1S)-5-amino-1-carboxypentyl]-carbamoyl]ethyl]dithio]ethyl]mitomycin C |
| 24 | 7-N-[2-[[2-[[(1S)-4-amino-1-carboxybutyl]-carbamoyl]ethyl]dithio]ethyl]mitomycin D |
| 25 | 7-N-[2-[[2-[[(1S)-5-amino-1-carboxypentyl]-carbamoyl]ethyl]dithio]ethyl]mitomycin D |
| 26 | 7-N-[2-[[[[17β-(3-benzoyloxy-1, 3, 5(10)-estra-trienyl)oxy]carbonyl]methyl]dithio]ethyl]mitomycin C |
| 27 | 7-N-[2-[[2-[[17β-(3-benzoyloxy-1, 3, 5(10)-estra-trienyl)oxy]carbonyl]ethyl]dithio]ethyl]mitomycin C |
| 28 | 7-N-[2-[[[[17β-(3-benzoyloxy-1, 3, 5(10)-estratrienyl)-oxy]carbonyl]methyl]dithio]ethyl]mitomycin D |
| 29 | 7-N-[2-[[2-[[(ethoxycarbonyl)methyl]carbamoyl]-ethyl]dithio]ethyl]mitomycin C |
| 30 | 7-N-[2-[[1-[[(ethoxycarbonyl)methyl]carbamoyl]-ethyl]dithio]ethyl]mitomycin C |
| 31 | 7-N-[2-[[2-[[2-(3, 4-dihydroxyphenyl)ethyl]-carbamoyl]ethyl]dithio]ethyl]mitomycin C |
| 32 | 7-N-[2-[[2-[(2S)-2-(3, 4-dihydroxyphenyl)-2-hydroxy]-ethyl]dithio]ethyl]mitomycin C |
| 33 | 7-N-[2-[[2-(acetylthio)ethyl]dithio]ethyl]-mitomycin C |
| 34 | 7-N-[2-[[2-(acetylthio)ethyl]dithio]ethyl]-mitomycin D |
| 35 | 7-N-[2-[[2-(retinoyloxy)ethyl]dithio]ethyl]-mitomycin C |
| 36 | 7-N-[2-[(2-sulfoethyl)dithio]ethyl]mitomycin C (as sodium salt) |
| 37 | 7-N-[2-[[(2, 4-dioxopyrimidin-5-yl)methyl]dithio]-ethyl]mitomycin C |
| 38 | 7-N-[2-[[(2, 4-dioxopyrimidin-5-yl)methyl]dithio]-ethyl]mitomycin D |
| 39 | 7-N-[2-[[(2'-deoxyuridin-5-yl)methyl]dithio]-ethyl]mitomycin C |
| 40 | 7-N-[2-[[(2'-deoxyuridin-5-yl)methyl]dithio]-ethyl]mitomycin D |

TABLE 2

$$X-(CX'X'')_n-SS(CH_2)_2NH-\text{[mitomycin core with }R_1, R_2, OY, NZ\text{ substituents]}$$

| No. | $X-(CX'X'')_n$ | $R_1$ | $R_2$ | Y | Z |
|---|---|---|---|---|---|
| 1 | L-γ-Glu-NH-CH₂– (HOOC-CH(NH₂)-CH₂-CH₂-C(O)-NH-CH₂–) ** | CH₂OCONH₂ | H | Me | H |
| 2 | " | H | CH₂OCONH₂ | H | Me |
| 3 | D-γ-Glu-NH-CH₂– | CH₂OCONH₂ | H | Me | H |
| 4 | L-γ-Glu-NH-(CH₂)₂-CH₂– | CH₂OCONH₂ | H | Me | H |
| 5 | L-γ-Glu-NH-(CH₂)₃-CH₂– | " | " | " | " |
| 6 | L-Asn-CH₂– (HOOC-CH(NH₂)-CH₂-C(O)-NH-CH₂–) | " | " | " | " |
| 7 | D-Asn-CH₂– | " | " | " | " |
| 8 | L-pyroGlu-NH-CH₂– | CH₂OCONH₂ | H | Me | H |
| 9 | L-iso-Glu-NH-CH₂– (HOOC-CH₂-CH₂-CH(NH₂)-C(O)-NH-CH₂–) | " | " | " | " |
| 10 | L-Asn-CH₂– | H | CH₂OCONH₂ | H | Me |
| 11 | L-γ-Glu-NH-CH₂– | " | " | " | " |
| 12 | L-pyroGlu-NH-CH₂– | H | CH₂OCONH₂ | H | Me |
| 13 | L-Pro-NH-CH₂– | CH₂OCONH₂ | H | Me | H |

TABLE 2-continued

X—(CX'X")ₙ—SS(CH₂)₂NH— [quinone-pyrrolidine core with R₁, R₂, OY, NZ substituents and CH₃ group]

| No. | X—(CX'X")ₙ | R₁ | R₂ | Y | Z |
|-----|------------|-----|-----|---|---|
| 14  | [uracil-acrylamide-CH₂– structure] | " | " | " | " |
| 15  | [retinoyl-NH-CH₂– structure] | " | " | " | " |
| 16  | [tocopherol succinate-NH-CH₂– structure] | CH₂OCONH₂ | H | Me | H |
| 17  | CH₃C(O)NH-CH₂– | H | CH₂OCONH₂ | H | Me |
| 18  | HC(O)NH-CH₂– | H | CH₂OCONH₂ | H | Me |
| 19  | CF₃C(O)NH-CH₂– | CH₂OCONH₂ | H | Me | H |
| 20  | CF₃C(O)NH-CH₂– | H | CH₂OCONH₂ | H | Me |
| 21  | H₂N-C(O)-CH₂– | CH₂OCONH₂ | H | Me | H |
| 22  | [diaminobutyric acid-NH-C(O)-CH₂– structure] | " | " | " | " |
| 23  | [ornithine-NH-C(O)-CH₂– structure] | " | " | " | " |
| 24  | [ornithine-NH-C(O)-CH₂– structure] | H | CH₂OCONH₂ | H | Me |

TABLE 2-continued

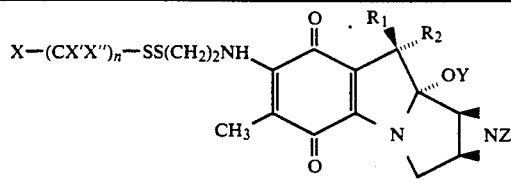

| No. | X—(CX'X")n | R1 | R2 | Y | Z |
|-----|------------|----|----|---|---|
| 25 | (ornithine-propionyl group) | H | CH$_2$OCONH$_2$ | H | Me |
| 26 | (estradiol 3-benzoate 17-acetyl-CH$_2$—) | CH$_2$OCONH$_2$ | H | Me | H |
| 27 | (estradiol 3-benzoate 17-propionyl-CH$_2$—) | " | " | " | " |
| 28 | (estradiol 3-benzoate 17-acetyl-CH$_2$—) | H | CH$_2$OCONH$_2$ | H | Me |
| 29 | EtO-CO-CH$_2$-NH-CO-CH$_2$— | CH$_2$OCONH$_2$ | H | Me | H |
| 30 | EtO-CO-CH$_2$-NH-CO-CH(CH$_3$)— | " | " | " | " |
| 31 | (3,4-dihydroxyphenyl)-CH$_2$CH$_2$-NH-CO-CH$_2$— | " | " | " | " |
| 32 | (3,4-dihydroxyphenyl)-CH(OH)-CH$_2$-NH-CO-CH$_2$— | CH$_2$OCONH$_2$ | H | Me | H |
| 33 | CH$_3$-CO-S-CH$_2$— | " | " | " | " |

TABLE 2-continued

X—(CX'X")n—SS(CH2)2NH— [quinone-pyrrolidine structure with R1, R2, OY, NZ, CH3]

| No. | X—(CX'X")n | R1 | R2 | Y | Z |
|---|---|---|---|---|---|
| 34 | CH3-C(=O)-S-CH2– | H | CH2OCONH2 | H | Me |
| 35 | [retinoyl ethyl ester-CH2–] | CH2OCONH2 | H | Me | H |
| 36 | NaO3S-CH2– | CH2OCONH2 | H | Me | H |
| 37 | [thymine-5-CH2–] | " | " | " | " |
| 38 | [thymine-5-CH2–] | H | CH2OCONH2 | H | Me |
| 39 | [thymidine-5-CH2–] | CH2OCONH2 | H | Me | H |
| 40 | [thymidine-5-CH2–] | H | CH2OCONH2 | H | Me |

**in some cases described hereinafter, this is referred to as "Q".
Notes:
Me: CH3
Et: C2H5

Compounds I may be obtained by following three processes classified into Processes A, B and C.

PROCESS A

Compound I may be prepared by the reaction of a compound of the formula (II):

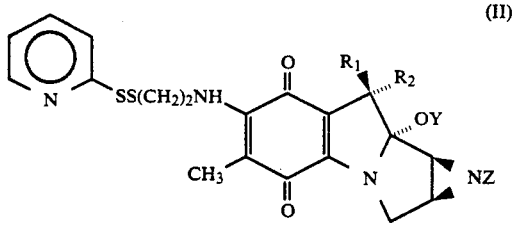
(II)

(wherein $R_1$, $R_2$, Y and Z are as hereinbefore defined) with a compound of the formula (III):

$$X-(CX'X'')_n SH \qquad (III)$$

(wherein X, X', X'' and n are as hereinbefore defined) in an inert solvent.

Compounds represented by the formula (II) are disclosed in EP 0116208A1 and Japanese laid open Patent Application 175493/84.

Solvents which may be used for this reaction are exemplified by halogenated lower alkanes such as chloroform and dichloromethane; lower alkanols such as methanol, ethanol and isopropanol; tetrahydrofuran, ethylene glycol dimethylether, dioxane, acetonitrile, dimethylformamide, dimethyl sulfoxide and water, which may be used solely or in combination. The reaction temperature and the reaction time may vary, depending upon the types of Compounds III. However, usually, it is possible to carry out the reaction at a temperature of from 0° to 30° C. for a period of several minutes to several hours.

Compounds I may be purified, for example, by column chromatography, high performance liquid chromatography and TLC, for which various carriers may be used.

The above-mentioned process is hereinafter referred to as Process A.

Compounds III containing $R_3NH$ as X, of which $R_3$ is the structural component of an α-amino acid, from which OH of the carboxyl group is excluded, are new compounds and may be obtained, for example, by Process (A-1) or (A-2) as follows:

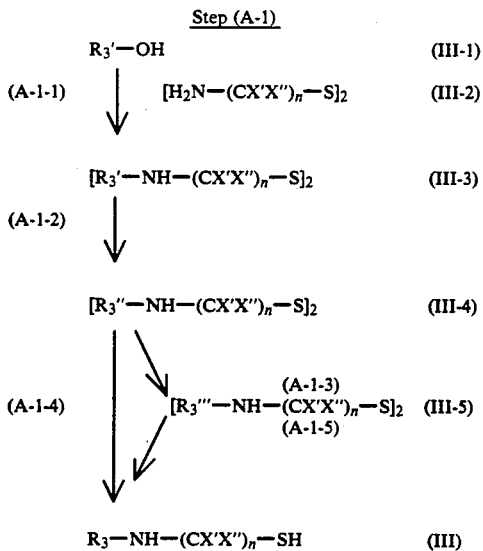

[wherein $R_3'$ is the structural component of an α-amino acid, from which OH of the carboxyl group is excluded; the amino group is be protected by a group used conventionally for the protection in the synthesis of peptides;

provided that when said α-amino acid has two carboxyl groups, one of the carboxyl groups is protected by a group conventionally used for the protection in the synthesis of peptides; optionally, the functional group of the side chain may also be protected;

$R_3''$ is the structural component of an amino acid, from which OH of the carboxyl group is excluded (wherein all protective groups are removed);

$R_3'''$ is the structural component of an α-amino acid, from which OH of the carboxyl group is excluded; provided that said α-amino acid has an amino group and a carboxyl group, said amino group is protected by lower alkanoyl and/or said carboxyl group is protected by lower alkyl;

X, X'' and n are as hereinbefore defined].

With regard to the definition of said $R_3'$, suitable groups conventionally used for the protection of amino group are exemplified by benzyloxycarbonyl and t-butyloxycarbonyl.

Suitable examples of the groups conventionally used for the protection of carboxyl group in the synthesis of peptides include benzyl and t-butyl groups.

The above-mentioned process steps (A-1-1)-(A-1-5) are described in detail hereinafter.

Step (A-1-1)

Compounds III-1 and III-2 are condensed in conventional manner used for the synthesis of peptides such as, for example, by the active ester method and the acid chloride method. The former is exemplified in the following, with reference to N,N-dicyclohexylcarbodiimide (hereinafter referred to as DCC) additive method.

To an inert solvent such as, for example, dichloromethane, chloroform, tetrahydrofuran, dioxane and dimethylformamide containing Compound III-1 may be added about an equimolar amount of a condensing agent such as, for example, DCC and an equimolar amount of N-hydroxysuccinimide or 1-hydroxybenzotriazole. The reaction may be carried out at a temperature of 0° C. to ambient for a period of from several hours to abut 12 hours to obtain an active ester. Subsequently, to the reaction solution is added Compound III-2. The reaction may be effected at a temperature of 0° C. to ambient for a period of several tens of minutes to several hours to obtain Compound III-3. If desired, the active ester may be isolated, purified and used for the reaction with Compound III-2. The resultant Compound III-3 may be purified, for example, by recrystallization, chromatographic treatment using, for example, silica gel and alumina.

N,N'-bis-[N-benzyloxycarbonyl-γ-(α-benzyl)-L-glutamyl]cystamine, which is one of the examples of Compound III-3 is disclosed by Laszlo Feuer et al in Japanese laid open Patent Application 4121/76 and DE 1518160.

Step (A-1-2)

The groups used for the protection of $R_3'$ may be removed, for example, by the use of trifluoroacetic acid, trifluoromethanesulfonic acid or hydrofluoric acid in conventional manner.

In the case of Compound III-3 where the amino group and the carboxyl group are respectively protected by benzyloxycarbonyl and benzyl, the protecting groups may be removed by using 1 to 10 molar equivalents of trifluoromethanesulfonic acid in the presence of the same molar amount of anisole or thioanisole. The reaction may be effected at a temperature of from 0° C. to ambient for a period of several minutes to several hours in dichloromethane or trifluoromethane.

In the case of Compound III-3 where the amino group and the carboxyl groups are respectively protected by t-butyloxycarbonyl and t-butyl, the protecting groups may be removed by the reaction using trifluoroacetic acid or trifluoroacetic acid-dichloromethane. The reaction may be effected in a similar manner to that described above. The resultant Compound III-4 may be purified, for example, by recrystallization, ion exchange method and various chromatographic treatments.

Step (A-1-3)

To obtain Compound III-5 from Compound III-4, the amino group of Compound III-4 may be protected by lower alkanoyl. Also, where carboxyl is present therein, the carboxyl may be protected as lower alkylester.

The amino group may be protected by lower alkanoyl by the reaction of an equimolar amount of an alkanoyl halide or a corresponding acid anhydride in the presence of a slightly excessive amount of potassium hydroxide, sodium hydroxide or sodium bicarbonate in an aqueous solution of Compound III-4, which may be effected at a temperature of from 0° C. to ambient for a period of from several tens of minutes to several hours. The carboxyl group may be converted into the corresponding lower alkyl ester, for example, by the thionyl chloride method, the azeotropic method or the ester exchange method. In the case of thionyl chloride method, a slightly excessive amount of thionyl chloride is added to said lower alkanol solution containing Compound III-4 to carry out the reaction at a temperature of from 0° C. to ambient for a period of from several hours to one day. The resultant Compound III-5 may be purified, for example, by recrystallization and ion-exchange method and chromatographic treatments including reversed phase high performance liquid chromatography using chemical-coupling type silica as carrier.

Steps (A-1-4) and (A-1-5)

Compound III-4 and III-5 may be converted into Compound III, for example, by the reaction with an excessive amount of ethanethiol, 2-mercaptoethanol or dithiothreitol in a solvent such as, for example, water, methanol, ethanol, tetrahydrofuran, dioxane, acetonitrile and dimethylformamide at room temperature for a period of from several hours to several days. Compound III may be purified, for example, by recrystallization, ion-exchange method an chromatographic treatments such as, for example, reversed phase high performance liquid chromatography using chemical-coupling type porous silica as carrier.

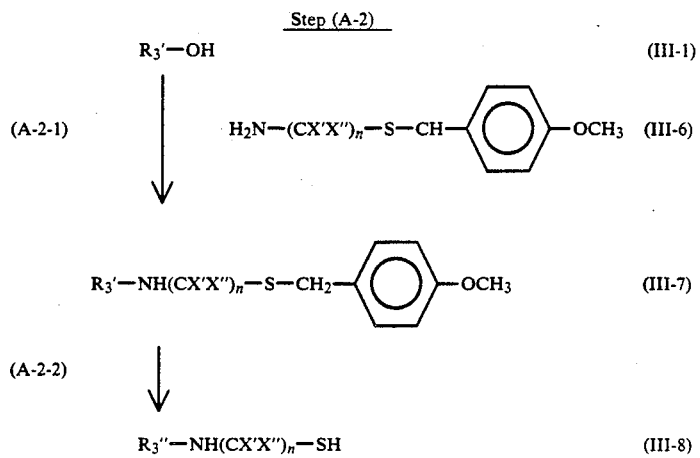

[wherein $R_3'$, $R_3''$, $X'$ and $X''$ and n are as hereinbefore defined].

Step (A-2-1)

Compounds III-1 and III-6 are subjected to a similar condensation to that described in Step (A-1-1) to obtain Compound III-7.

Compounds III-6 are exemplified by 2-[(p-methoxybenzyl)thio]ethylamine. This compound and its preparation are disclosed in Armyanskii Khimicheskii Zhurnal, 1968, 21 (10), 858–863.

Step (A-2-2)

Compounds III-8 may be obtained, for example, by the use of trifluoromethanesulfonic acid/anisole, trifluoromethanesulfonic acid/thioanisole or hydrogen fluoride for removal of group used for the protection of the amino group of $R_3'$, and/or the group used for the protection of the carboxyl group of $R_3'$, if any carboxyl group is protected. The methoxybenzyl group linked with sulphur may also be treated similarly.

Compounds III-8 may be prepared, for example, in the following manner. On the basis of Compound III-7, 1–10 molar equivalents of trifluoromethanesulfonic acid may be used. The reaction may be effected in the presence of the same molar amount of anisole or thioanisole in trifluoroacetic acid or trifluoroacetic acid/dichloromethane at a temperature of from 0° C. to room temperature for a period of from several tens of minutes to several hours. It is also possible to remove the protecting groups by the reaction in a solution of hydrogen fluoride in the presence of 1/10 amount of anisole at a temperature of about 0° C. for a period of 30–60 minutes. Compounds III-8 may be purified, for example, by recrystallization, ion-exchange method and chromatographic treatments including high performance liquid chromatography using chemical-coupling type porous silica as carrier.

Compound III, of which X is

and $R_4$ is the structural component of an α-amino acid, from which H of the amino group is excluded, are new compounds and may be obtained by the following Step (A-3).

Step (A-3)

$R_4'H$      (III-9)

(A-3-1) ↓ $[HOOC-(CX'X'')_nS]_2$      (III-10)

$[R_4'-\overset{O}{\underset{\|}{C}}-(CX'X'')_nS]_2$      (III-11)

(A-3-2) ↓

$[R_4''-\overset{O}{\underset{\|}{C}}-(CX'X'')_nS]_2$      (III-12)

↘ (A-3-3)

(A-3-4)   $[R_4'''-\overset{O}{\underset{\|}{C}}-(CX'X'')_nS]_2$      (III-13)

↓ ↙ (A-3-5)

$R_4-\overset{O}{\underset{\|}{C}}-(CX'X'')_n-SH$      (III)

[wherein
- $R_4'$ is the structural component of an α-amino acid, from which H of the amino group is excluded; a carboxyl group is protected by a group conventionally used for the protection in the synthesis of peptides; provided that said α-amino acid has two amino groups, one of them is protected by a group conventionally used for the protection in the synthesis of peptides;
- $R_4''$ is the structural component of an α-amino acid, from which H of the amino group is excluded (wherein all protecting groups are removed);
- $R_4'''$ is the structural component of an α-amino acid, from which H of the amino group is excluded; provided that said structural component has an amino group or one or two carboxyl group, said carboxyl group is protected as a lower alkyl ester or said amino group is protected by a lower alkanoyl;
- $X'$, $X''$ and n are as hereinbefore defined].

With regard to the definition of the above-mentioned $R_4'$, the groups conventionally used for the protection of amino groups in the synthesis of peptides are exemplified by benzyloxycarbonyl and t-butyloxycarbonyl groups, whilst preferred examples of the groups conventionally used for the protection of carboxyl group in the synthesis of peptides include benzyl and t-butyl groups.

Although Steps (A-3-1) to (A-3-5) are similar to Steps (A-1-1) to (A-1-5), Step (A-3-1) is different from Step (A-1-1) with respect to the following:

In Step (A-1-1), the carboxyl group of $R_3OH$, viz. a derivative of α-amino acid is activated, whilst in Step (A-3-1), Compound III-10 is activated to condense with the amino group of $R_4'H$, which is a derivative of the amino acid. Other aspects of Steps (A-3-1) to (A-3-5) are similar to those of Steps (A-1-1) to (A-1-5).

Compound III containing $R_3$ selected from formyl, lower alkanoyl and halogen-substituted lower alkanoyl, may readily be prepared by treating a compound of the formula:

$$H_2N(X'X'')_n-SH \quad\quad (III-14)$$

(wherein X', X'' and n are as hereinbefore defined) with a suitable compound containing formyl, lower alkanoyl or halogen-substituted lower alkanoyl or by the acyl rearrangement of a compound of the formula:

$$HN_2(CX'X'')_n-SR_3'''' \quad\quad (III-15)$$

(wherein $R_3''''$ is lower alkanoyl or halogen-substituted lower alkanoyl; and X', X'' and n are as hereinbefore defined) in an inert solvent.

For example, $$H_2N(CH_2)_2S\overset{O}{\underset{\|}{C}}CH_3 \cdot HCl$$

viz. 2-acetylthioethylamine hydrochloride is disclosed in Journal of Chemical Society, 3425 (1951); 5-mercaptomethyluracil which is one of the Compounds III is disclosed in Journal of Medicinal Chemistry, 9, 97 (1951); and 1-(2-deoxy-β-D-ribofuranosyl)-5-mercaptomethyluracil is disclosed in ibid., 18, 973 (1975).

Process B is explained as follows:

PROCESS B

Compound 1 may be obtained by reacting a compound of the formula IV:

[Structure IV: a quinone ring with $CH_3O$ and $CH_3$ substituents, fused to a pyrrolidine ring bearing $R_1$, $R_2$, OY and NZ groups]

(wherein $R_1$, $R_2$, Y and Z are as hereinbefore defined) such as, for example, mitomycin A, mitomycin B [disclosed in Merck Index, 10th Edition, 6079 (1983)] or mitomycin J (disclosed in Japanese laid open Patent Application 45322/80) with a compound of the formula V:

$$X-(CX'X'')_n-SS(CH_2)_2NH_2 \quad\quad (V)$$

(wherein X, X', X'' and n are as hereinbefore defined) in an inert solvent.

This process is hereinafter referred to as Process B.

The solvents which may be used for the above-mentioned Process A may be used for this process. The reaction temperature and the reaction time may vary, depending upon the type and concentration of Compound V used. Usually it is sufficient to carry out the reaction at a temperature of from 0° to 80° C. for a period of several tens of minutes to several hours.

Compounds I may be purified, for example, by column chromatography, high performance liquid chromatography and TLC, for which various carriers may be used.

Compounds V may be obtained by the following Step (B-1) or (B-2)

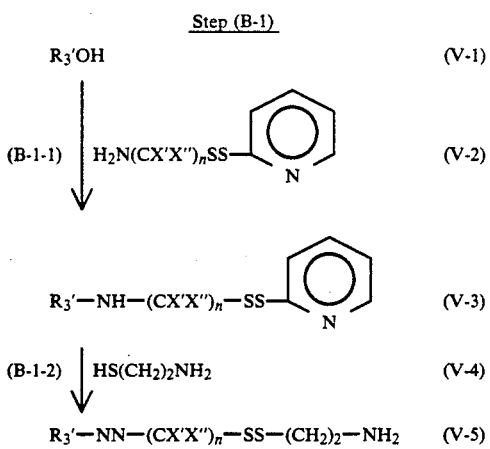

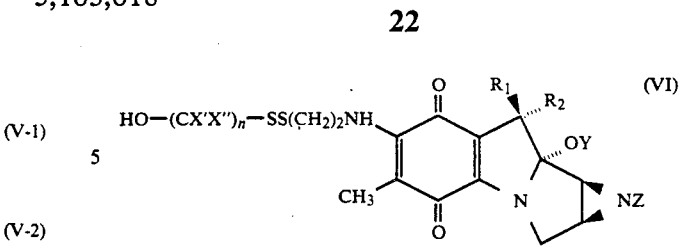

[wherein R₃' is the structural component of an organic acid, from which OH of the carboxyl group is excluded; X', X" and n are as hereinbefore defined].

Organic acids hereinbefore disclosed may be used for this procedure. Steps (B-1-1) and (B-1-2) may be carried out similarly to Steps (A-1-1) and Process A respectively.

Compounds V-2 are exemplified by 2-pyridyldithioethylamine (dihydrochlorides) disclosed in Japanese laid open Patent Application 136261/80.

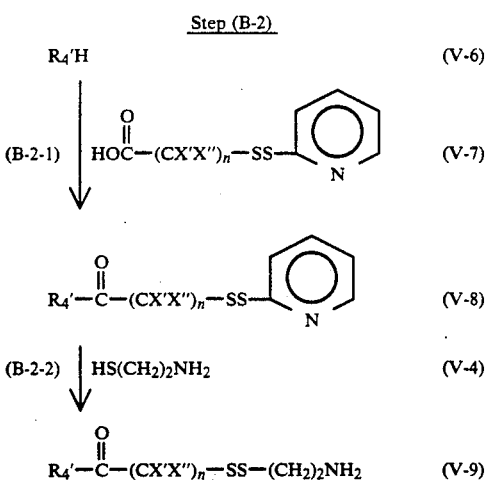

[wherein R₄' is the structural component of an organic amine, from which a hydrogen atom is excluded; and X', X" and n are as hereinbefore defined].

Organic amines described hereinbefore may be used for this purpose.

Steps (B-2-1) and (B-2-2) may be carried out similarly to Steps (A-1-1) and Process A respectively.

Examples of succinimidesters of the carboxylic acid of Compound V-7 include N-succinimidyl 3-(2-pyridyldithio)propionate (Sigma P9398).

Process C is described in detail as follows:
A compound of the formula (VI):

(wherein X', X", $R_1$, $R_2$, Y, Z and n are as hereinbefore defined) is reacted with a compound of the formula (VII):

$$R_3OH \text{ or } R_3SH \qquad (VII)$$

(wherein $R_3$ is as hereinbefore defined) in the presence of triphenylphosphine and dialkyl azodicarboxylate in an inert solvent to obtain the desired Compound I.

Compound (VI), of which X' and X" each represents H and n is 2, is disclosed in Japanese laid open Patent Application 175493/84.

Solvents which may be used for this reaction are exemplified by ether-type solvents such as diethylether and tetrahydrofuran; benzene, methylene chloride, hexamethyl-phosphorus triamide and other anhydrous solvents.

Examples of dialkyl azodicarboxylates include diethyl azodicarboxylate and diisopropyl azodicarboxylate.

For example, equimolar amounts of Compound VII, triphenylphosphine and dialkyl azodicarboxylate may be used on the basis of Compound VI, although it is possible, if desired, to use up to about 3 molar equivalents of each compound to improve the production yield.

The reaction temperature and the reaction time may vary, depending upon the types of Compounds VI and VII. However, usually it is possible to carry out the reaction at a temperature of from −20° to 30° C. for a period of from about several minutes to about one hour.

Although the treatment after the reaction may vary, depending upon the type of Compound VII used, for example, it is possible to concentrate the reaction solution without any after-treatment. Alternatively, the reaction solution may be extracted with water-insoluble solvent such as, for example, chloroform, methylene chloride or ethyl acetate, and washed with water, sodium bicarbonate solution, followed by concentration. The concentrated material may be purified, for example, by column chromatography, TLC and recrystallization.

Compounds I exhibit excellent anti-bacterial and anti-tumour activities and may be used as anti-bacterial and anti-tumour agents. In comparison with mitomycin C which is widely and clinically used as anti-tumour agent, Compounds I exhibit, in general, higher anti-tumour activity and lower bone marrow suppression. That is, Compounds I have better C.I. ($LD_{50}ED_{50}$) and wider tolerance of dosage, greater $WBC_{4000}$ (minimum dosage required to reduce the number of peripheral leucocytes to 4000/mm³) and lower bone marrow supression in comparison with mitomycin C.

Among water-soluble Compounds I, of which $R_3$ is the structural component of an amino acid, from which OH of the carboxyl group is excluded, those containing the structural component of glutamic acid or the structural component of aspartic acid exhibit better anti-tumour activity. Among such compounds, those of which n is an integer of from 2 to 4, exhibit, in general, high water-solubility and are suitable for the preparation of injection agents. Especially good results may be obtained by Compound 1, of which X is the structural component of glutamic acid substituted at the γ position; n is 2; $R_1$ is $CH_2OCONH_2$; $R_2=H$; $Y=CH_3$ and Z is H. The C.I. value ($LD_{50}/ED_{50}$) and ($WBC_{4000}/ED_{50}$) of this compound are very high and its water-solubility is good. In view of these characteristics, this compound is far superior to mitomycin C.

Lipophilic anti-tumour agents have recently become attractive. Lipophilic anthracyclin derivatives have been studied, [disclosed, for example, in Journal of Medicinal Chemistry, 28, 451 (1985)]. Also, lipophilic mitomycin derivatives have been studied [for example, Chemical and Pharmaceutical Bulletin, 31, 4083 (1983) and Journal of Pharmacobio-Dynamics, 7, 120 (1984)]. Such lipophilic derivatives are more suitable than hydrophilic derivatives for the chemotherapy using, for example, lipiodol Chemotherapy using anthracyclin dissolved in lipiodol is reported, for example, in Journal of Surgical Oncology, 25, 218 (1984).

Certain Compounds I exhibit high lipophilicity, high C.I. value and high $WBC_{4000}/ED_{50}$ value. With regard to these characteristics, for example, Compounds 26, 27 and 28 are superior to mitomycin C.

The following experiments reveal the pharmacological characteristics of Compounds I of the present invention.

EXPERIMENT 1

Certain Compounds I were selected. Table 3 indicates their anti-bacterial activities in terms of their minimum inhibitory concentration (μg/ml), determined by the agar dilution method effected at a pH of 7.0. In this table, the microorganisms used are abbreviated as follows:

SF: *Streptococcus faecalis* ATCC 10541
SA: *Staphylococcus aureus* ATCC 6583P
EC: *Escherichia coli* ATCC 26
PV: *Proteus vulgaris* ATCC 6897
KP: *Klebsiella pneumoniae* ATCC 10031

TABLE 3

| No. | SF | SA | EC | PV | KP |
| --- | --- | --- | --- | --- | --- |
| 1 | 1.6 | 0.8 | >50 | 0.8 | 0.4 |
| 2 | 100 | 50 | — | 25 | >100 |
| 3 | 3.1 | 1.6 | 50 | 0.8 | 0.8 |
| 4 | 3.1 | 1.6 | 250 | 3.1 | 0.8 |
| 5 | 1.6 | 1.6 | — | 1.6 | 0.8 |
| 6 | 3.1 | 0.8 | >50 | 0.8 | 0.8 |
| 7 | 0.8 | 0.4 | 2.5 | 0.8 | 0.4 |
| 15 | 0.63 | 0.078 | — | 1.3 | 2.5 |
| 17 | 25 | >50 | — | >50 | — |
| 21 | 1.3 | 0.63 | — | 5.0 | 1.3 |
| 33 | 0.039 | 0.078 | >40 | 0.63 | 0.63 |
| 35 | 10 | 5.0 | — | — | — |
| MM-C | 0.08 | 0.04 | 10 | 0.02 | 0.02 |

Note:
MM-C mitomycin C

EXPERIMENT 2

Certain compounds were selected from Compounds I. The following Table 4 indicates anti-tumour activity against Sarcoma 180 solid tumour ($ED_{50}$), acute toxicity ($LD_{50}$) and effects on the peripheral leucocytes ($WBC_{4000}$) of each compound.

TABLE 4

| No. | $LD_{50}$ ip (mg/kg) | $ED_{50}$ ip (mg/kg) | (C.I.)* | ($WBC_{4000}/ED_{50}$)* |
| --- | --- | --- | --- | --- |
| 1 | 22.5 | 2.7 | 2.58 | 4.12 |
| 2 | 90.0 | 18 | 1.55 | 2.14 |
| 3 | 22.5 | 5.7 | 1.46 | 3.02 |
| 4 | 22.5 | 5.1 | 1.52 | 1.27 |
| 5 | 30.0 | 8.4 | 1.66 | 3.21 |
| 6 | 26.3 | 5.0 | 1.81 | 2.38 |
| 7 | 45.0 | 9.8 | 2.13 | 2.40 |
| 9 | 37.5 | 7.7 | 2.09 | 0.48 |
| 10 | 75.0 | 13.0 | 2.19 | 2.5 |
| 11 | 75.0 | 16.9 | 1.59 | 1.64 |
| 12 | 75.0 | 18.4 | 1.80 | 5.57 |
| 13 | 30.0 | 12.2* | 1.17* | 2.30* |
| 14 | 45.0 | 11.5 | 1.68 | 1.20 |
| 15 | 16.9 | 7.4* | 0.82* | 3.0* |
| 16 | >100 | 95.9* | >0.37* | 1.2* |
| 17 | 60.0 | 7.3 | 2.73 | 2.60 |
| 18 | 52.5 | 10.6 | 1.94 | 3.89 |
| 19 | 9.4 | 8.7 | 0.51 | >0.96 |
| 20 | 30.0 | 11.6 | 0.93 | 4.40 |
| 21 | 18.8 | 11.8 | 0.68 | 1.01 |
| 22 | 37.5 | 5.0 | 2.68 | 6.00 |
| 23 | 37.5 | 6.2 | 2.14 | 5.40 |
| 24 | >100 | 31.2 | >1.53 | 2.02 |
| 25 | >100 | 46.6 | >1.02 | 1.59 |
| 26 | 18.8 | 5.0 | 1.27 | 2.57 |
| 27 | 22.5 | 4.6 | 1.63 | 2.43 |
| 28 | 75.0 | 9.9 | 2.53 | 1.43 |
| 29 | 33.8 | 9.4 | 1.77 | 2.90 |
| 30 | 37.5 | 10.3 | 1.78 | 2.64 |
| 31 | 26.3 | 7.1 | 1.15 | 2.28 |
| 32 | 30.0 | 7.1 | 1.56 | 2.39 |
| 33 | 4.7 | 5.6* | 0.36* | 1.27 |
| 36 | 37.5 | 7.0 | 1.66 | 2.63 |
| 37 | 37.5 | 16.4 | 1.35 | 1.15 |
| 38 | >150 | 24.5 | >2.26 | >8.71 |
| 39 | 75.0 | 34.7 | 1.37 | 1.50 |
| 40 | ≧200 | 104* | 1.22* | 0.95 |
| MM-C 1 | 8.4 | 2.6–3.9 | 1 | 1 |
| MM-C 2 | <12.0 | 5.4 | 1.16 | 0.95 |

Notes:
MM-C 1 (mitomycin C)
MM-C 2 (albomitomycin C)
(C.I.)* = ($LD_{50}/ED_{50}$)/[($LD_{50}/ED_{50}$) of MM-C1].
($WBC_{4000}/ED_{50}$)* = ($WBC_{4000}/ED_{50}$)/[($WBC_{4000}/ED_{50}$) of MM-C1].
*External standard method.

It was previously known that there are two types of mitomycin A and mitomycin C viz. mitomycin-type and albomitomycin-type substances [cf. Abstracts, the 27th Symposium on the Chemistry of Natural Products pp. 672–679, (1985), Hiroshima]. As disclosed in Example 1 hereinafter, it has been found that these two types are also present in various mitomycin derivatives of the present invention.

The results shown in Table 4 were obtained by the following experiments:

(1) Effect against Sarcoma 180 solid tumour:

$5 \times 10^6$ cells of Sarcoma 180 solid tumour cells were abdominally implanted into male mice of ddy strain. 7 days after this, ascites cells were sampled. The cells were washed once with a sterilized physiological solution of sodium chloride and were used to prepare a cell suspension containing $5 \times 10^7$ cells per ml. On each occasion, 0.1 ml of the cell suspension was subcutaneously implanted into the right armpit of a male mouse (ddy strain; body weight 20±2 g). 24 hours after the implantation of the tumour cells, the test compound which was dissolved in a physiological solution of sodium chloride with or without addition of Tween 80 was abdominally administered to each mouse of a group consisting of 5 animals at a does of 0.1–0.2 ml. The anti-tumour activity was determined as follows:

7 days after the implantation, the major axis (a) and the minor axis (b) of the tumour were measured to calculate a value of "a×b²/2" which corresponds to the volume of the tumour. The anti-tumour activity was expressed by T/C viz. the ratio of the volume of the tumours (T) of the group of animals administered with the test compound to the corresponding volume of tumours (C) of the untreated animals.

(2) Determination of $ED_{50}$:

The term $ED_{50}$ denotes the administered amount needed for reducing the volume of Sarcoma 180 solid tumours in the animals to 50% on the basis of the corresponding volume of Sarcoma 180 solid tumours in control (untreated) animals.

On graph paper, T/C was indicated by an arithmetic scale on the longitudinal axis and the administered amount of test compound was indicated by a logarithmic scale on the lateral axis. The relationship between the dose and T/C was shown by a straight line determined by the method of least squares, from which a does corresponding to T/C of 0.5 was obtained.

(3) Acute toxicity:

Each animal of the test group consisting of 5 ddy mice was once administered (i.p.) with a test compound. After this, the animals were observed for 14 days to note the survival ratio. The $LD_{50}$ was determined by Behren Körber's method.

(4) Effect upon the number of the peripheral leucocytes:

Sarcoma 180 solid tumour cells ($5 \times 10^6$) were subcutaneously implanted into the right armpit of each mouse (body weight $20 \pm 2$ g) of a group consisting of 5 male mice (ddy strain). 24 hours after implantation, a test compound was abdominally administered to each mouse. 4 days later, blood (each 0.02 ml) was collected from the suborbital plexus vein of each tumour-carrying mouse. The collected sample of blood was dispersed in 9.98 ml of Cell-kit Seven solution. One drop of saponin solution was added to the sample to dissolve erythrocytes and then a microcell counter was used to measure the number of leucocytes. On graph paper, the number of leucocytes was indicated on the y-axis by an arithmetic scale and the does of the test compound was indicated on the x-axis by a logarithmic scale.

The relationship between the number of peripheral leucocytes and the dosage of the test compound was plotted to obtain $WBC_{4000}$ viz. the dosage corresponding to 400 peripheral leucocytes per mm³ (about half of the number of leucocytes of normal mice).

(5) Effect upon Leukemia P 388:

Ascites cells were collected from P388 Leukemia-carrying mouse (DBA/2) 7 days after the implantation. The number of the cells of P388 Leukemia in the sample was counted. A physiological solution of sodium chloride was sterilized and used to prepare a cell suspension containing $5 \times 10^6$ tumour cells per ml. On each occasion, 0.2 ml of the suspension containing $1 \times 10^6$ cells was implanted into the abdominal cavity of each mouse ($CDF_1$; body weight 20~25 g). 24 hours after implantation, the test compound was once given to each mouse of a test group consisting of 6 mice by abdominal injection.

Survival days of all animals were observed for a period of 33 days. The activity of the test samples was determined by the ratio of the average survival days of the treated animals to the average survival days of untreated animals viz. ILS % (Increased Life Span).

Table 5 indicates ILS* which is the ratio of ILS % of each of various test compounds to the corresponding ILS % obtained by using mitomycin C as control under the same condition.

TABLE 5

| No. | ILS | Dose (mg/kg) |
|---|---|---|
| 1 | >2.30 | 25 |
| 2 | >1.34 | 50 |
| 14 | >2.60 | 20.3 |
| 17 | >1.78 | 25 |
| 26 | >1.08 | 6.25 |
| 27 | >1.53 | 12.5 |
| 28 | >1.67 | 25 |
| 30 | 2.14 | 25 |
| 32 | >1.44 | 3.13 |
| 37 | 1.69 | 20 |
| 39 | 1.83 | 50 |

The present invention provides an anti-tumour composition, comprising as active ingredient an effective amount of Compound I. The compound may be used, for example, for injection by dissolving in a physiological solution of sodium chloride, injection solutions of glucose, lactose or mannitol. If desired, the compound may be formulated into a freeze-dried injection agent or injection powder by mixing with sodium chloride according to the Japanese Pharmacopoeia. The composition may contain pharmaceutically acceptable salts, for example, Ringer's solution, additives well-known in the art [e.g. polyethylene glycol, HCO-60 (surfactant, commercial product of Nikko Chemicals K.K., Japan], ethanol and/or carriers (e.g. ribosome and cyclodextrin). Although the does may vary, depending upon the ages and symptoms of patients, it is possible to administer to humans, for example, once to three times per week at a does of 0.06 to 6 mg/kg usually by intravenous injection. If desired, it is possible to administer the same amount into the artery, abdominal cavity or thorax cavity by injection. It is also possible to administer by oral or rectal route. In such cases, the compound may be added to suitable additives and formulated into tablets, powders, granules, syrups, suppositories and the like. The compounds have, in general, higher water-solubility or lipophilicity and lower toxicity than mitomycin C so that it is possible to provide excellent anti-tumour compositions.

BEST MODE EMBODIMENTS FOR CARRYING OUT THE INVENTION

The following examples and references illustrate the present invention, in which the physico-chemical characteristics were determined by means of the following instruments:

IR: JASCO IR-810 (commercial product of Nihon Bunkou K.K., Japan)

NMR: Bruker AM400, (Varian EM 390 and JEOL FX 100

MS: Hitachi M-80B (commercial product of Hitachi Seisakusho, Japan)

Optical rotation: Perkin-Elmer 141 Polarimeter

EXAMPLE 1

503 mg of 7-N-[2-(2-pyridyl)dithioethyl]mitomycin C (disclosed in EP 0116208A1 and Japanese laid open Patent Application 175493/84) was dissolved in 15 ml of methanol. An aqueous solution (15 ml) containing 200 mg of γ-L-glutamylcysteamine prepared by the method described in Reference 2 hereinafter was dropwise added to the starting material with stirring at room temperature. Water (120 ml) was then added thereto. The resultant reaction solution was applied to a column packed with Diaion HP-20 (100 ml; commercial product of Mitsubishi Kasei Kogyo K.K., Japan). Elution was effected by the use of a solvent system of water/methanol (300 ml; 7:3 v/v). A further elution was effected using a solvent system of water/methanol (300 ml; 4:6 v/v) to give blue fractions.

The blue fraction was concentrated under reduced pressure, followed by freeze-drying to obtain Compound 1 (263 mg) with a yield of 44%. The resultant product was a mixture of mitomycin-type (A) and albomitomycin-type (B) substances at a molar ratio of 95:5.

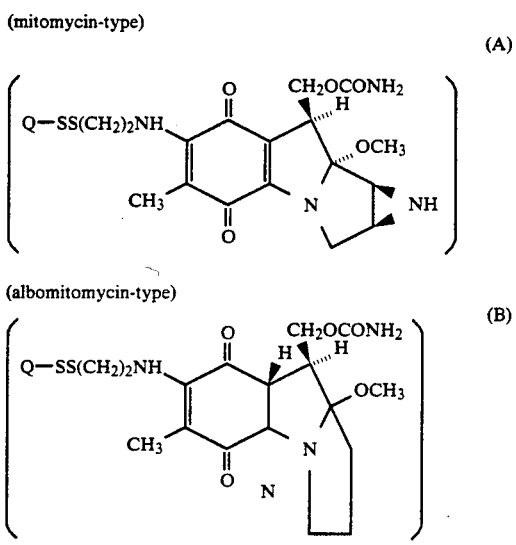

Compound 1 exhibited the following physico-chemical characteristics:

SIMS: m/s 599(M+1)+, 600 (M+2)+, 601 (M+3)+ (Molecular formula $C_{24}H_{34}N_6O_8S_2$; M.W. 598.7).

By the SIMS method, the ionization is made by collision of XE+ with the sample mixed with glycerol. In such cases, the quinone moiety of mitomycin is reduced by the action of the hydrogen radical originating from glycerol so that the mass number of the compound of the present invention may increase by 2. Moreover, there is a possibility of adding hydrogen ion and hydrogen radical to the target, as sometimes found in the case of usual EI mass spectrometry. Thus, the molecular formulae of the compounds of the present invention are highly credible on the ground that (M+2)+ and (M+3)+ ions were observed (a similar example is disclosed in Japanese laid open Patent Application as 33880/85).

| Elemental analysis: as $C_{24}H_{34}N_6O_8S_2 \cdot H_2O$ | | | |
|---|---|---|---|
| | C (%) | H (%) | N (%) |
| Calculated | 46.74 | 5.88 | 13.63 |
| Found | 46.51 | 5.97 | 13.60 |

$^1$H-NMR (400 MHz): D$_2$O δ 1.94* (s), 2.00 (3H, s), 2.15 (2H, m), 2.44 (2H, m), 2.86 (2H, t, J=6.3 Hz), 3.00 (2H, t, J=6.3 Hz), 3.02 (1H, br.), 3.05 (1H, br.), 3.30 (3H, s), 3.45*(s), 3.53 (2H, t, J=6.3 Hz), 3.65 (1H, br.d), 3.65 (1H, dd, J=10.7, 4.5 Hz), 3.78 (2H, t, J=6.2 Hz), 4.00 (2H, t, J=6.3 Hz), 4.19 (1H, br, d, J=13.7 Hz), 4.26 (1H, t, J=10.7 Hz), 4.60 (1H, dd, J=10.7, 4.5 Hz).

[Note: In this specification, $^1$H-NMR marked with * denotes a signal originating from albomitomycin-type substance]

IR: (KBr)cm$^{-1}$ 3450, 3300, 3080, 2950, 1707, 1631, 1560, 1510, 1460, 1328, 1062.

Solubility in water: >20 mg/ml.

A highly purified mitomycin-type Compound 1 was obtained in the following manner:

Compound 1 (45 mg; powders) was dissolved in 1.8 ml of distilled water. The solution was applied to preparative high performance liquid chromatography using a column packed with a carrier YMC D-ODS-7 (commercial product of Yamamura Kagaku K.K., Japan). Elution was effected by using a solvent system of water/acetonitrile (3:1 v/v) at a flow rate of 9.6 ml per minute. Blue fractions which were observed 11.7-13.5 minutes after the beginning of elution were collected and combined.

The combined fractions were freeze-dried to obtain grayish blue powders (33 mg). The resultant powders were subjected to high performance liquid chromatography using a column packed with UMC AM-312 (commercial product of Yamamura Kagaku K.K., Japan) and a solvent system of water/methanol (1:1 v/v). Elution was effected at a flow rate of 1 ml per minute. At a retention time of 6.0 minute, a single peak at 254 nm and a ratio of a real strength of >99% were noted. The resultant mitomycin-type compound showed the following physico-chemical characteristics:

SIMS: m/z 599 (M+1)+, 600 (M+2)+, 601 (M+3)+ (molecular formula $C_{24}H_{54}N_6O_8S_2$; M.W. 598.7)

$^1$H-NMR (400 MHz): (D$_2$O) δ 2.00 (3H, s), 2.15 (2H, m), 2.44 (2H, m), 2.86 (2H, t, J=6.3 Hz), 3.00 (2H, t, J=6.3 Hz), 3.02 (1H, br.), 3.05 (1H, br.), 3.30 (3H, s), 3.53 (2H, t, J=6.3 Hz), 3.65 (1H, br. d), 3.65 (1H, dd, J=10.7, 4.5 Hz,3.78 (2H, t, J=6.2 Hz), 4.00 (2H, t, J=6.3 Hz), 4.19 (1H, br.d, J=13.7 Hz), 4.26 (1H, t, J=10.7 Hz), 4.60 (1H, dd, J=10.7, 4.5 Hz).

IR: (KBr)cm$^{-1}$ 3450, 3300, 3080, 2950, 1707, 1631, 1560, 1510, 1460, 1328, 1062.

A highly purified albomitomycin-type compound was obtained in the following manner:

7.8~8.4 minutes after the beginning of the above-mentioned preparative high performance liquid chromatography, colourless fractions were eluted. The collected fractions were immediately frozen using dry ice/acetone to give slightly blueish powders (1.5 mg). The resultant powders were determined in a similar manner to that described above to give a main peak at a retention time of 4.2 minutes. There was obtained a ratio of a real strength of 95%.

The physico-chemical characteristics of this compound were as follows:

SIMS:m/z 599 (M+1)+.

$^1$H-NMR (400 MHz): (D$_2$O) δ 1.92 (3H, s), 2.14 (2H, m), 2.43 (2H, m), 2.70 (1H, d), 2.84 (1H, d) 2.85 (2H, m), 2.95 (1H, d), 3.00 (2H, m) 3.02 (1H, d), 3.44 (3H, s,), 3.51 (2H, m.), 3.53 (2H, t), 3.76 (1H, t), 3.82 (1H, m), 3.94 (1H, m), 4.31 (1H, dd), 4.41 (1H, dd).

IR: (KBr)cm$^{-1}$ 3400, 3350, 3080, 2950, 1705, 1630, 1570, 1510, 1450, 1400, 1335, 1240.

EXAMPLE 2

A similar treatment to that described in Example 1 was carried out except the use of 7-N-[2-(2-pyridyl)dithioethyl]mitomycin D (503 mg) disclosed in EP 0116208A1 and Japanese laid open Patent Application 175493/84) instead of 7N-[2-(2-pyridyl)dithioethyl]-mitomycin C to obtain 275 mg of Compound 2 with a yield of 46%.

The physico-chemical characteristics of the resultant compound were as follows:

SIMS:m/z 599 (M+1)$^+$, 600 (M+2)$^+$, 601 (M+3)$^+$ (Molecular formula $C_{24}H_{34}N_6O_8S_2$; M.W. 598.7).

As discussed in Example 1, these data make the molecular formula of this compound highly credible.

| Elemental analysis: as $C_{24}H_{34}N_6O_8S_2 \cdot H_2O$ | | | |
|---|---|---|---|
| | C (%) | H (%) | N (%) |
| Calculated | 46.74 | 5.88 | 13.63 |
| Found | 46.59 | 5.82 | 13.39 |

$^1$H-NMR (400 MHz): ($D_2O$) δ 1.98 (3H,s), 2.11 (2H, m), 2.30 (3H, s), 2.42 (2H, m), 2.60 (1H, d, J=4.9 Hz), 2.70 (1H, dd, J=4.9, 2.0 Hz), 2.84 (2H, t, J=6.2 Hz), 3.00 (2H, t, J=6.3 Hz), 3.51 (2H, t, J=6.3 Hz), 3.65 (1H, dd, J=13.7, 2.1 Hz), 3.73 (1H, dd, J&32 9.3, 3.6 Hz), 3.75 (1H, t, J=6.2 Hz), 4.02 (2H, t, J=6.3 Hz), 4.08 (1H, d, J=13.6 Hz), 4.40 (1H, dd, J=10.9, 9.3 Hz), 4.68 (1H, dd, J=10.9, 3.6 Hz)).

IR: (KBr)cm$^{-1}$ 3410, 3300, 3100, 2950, 1705, 1629, 1545, 1509, 1467, 1412, 1333.

Solubility in water: >5 mg/ml.

EXAMPLES 3-13

Compounds 3-13 were respectively obtained in a similar manner to that described in Example 1. SIMS, IR and $^1$H-NMR of each compound are shown in Table 6 hereinafter. Although all compounds are soluble in water, Compounds 3, 4, 5, 6, 7 and 9 exhibited a water-solubility of >20 mg/ml.

Table 6-2 indicates the molar ratio of mitomycin-type substance (A) to albomitomycin-type substance (B), which were isolated from each of Compounds 3 to 9.

TABLE 6

| Compound | A | B |
|---|---|---|
| 3 | 94 | 6 |
| 4 | 87 | 13 |
| 5 | 96 | 4 |
| 6 | 96 | 4 |
| 7 | 92 | 8 |
| 8 | 95 | 5 |
| 9 | 97 | 3 |
| 13 | >99 | <1 |

EXAMPLE 14

Compound "1" (E1) was prepared by the process of Reference 6 described hereinafter (328 mg) and dissolved in dimethylformamide (8 ml). Cysteamine hydrochloride (116 mg) and triethylamine (140 μl) were added to this solution, followed by stirring at room temperature for 5 minutes. Then mitomycin A (345 mg) was added thereto. The mixture was stirred at room temperature for 24 hours. After addition of water (30 ml) to the reaction solution, extraction was effected by using chloroform (150 ml). The chloroform solution was dried by using sodium sulfate. The solvent was removed from the reaction solution by evaporation. The residual solution was subjected to column chromatagraphy using silica gel (30 ml; Wako C200). A solvent system of chloroform/methanol (100 ml, 9:1 v/v) was passed through the column. Then elution was effected using a solvent system of chloroform/methanol (200 ml, 8:2 v/v) and a further system of chloroform/methanol (200 m: 7:3 v/v). Blue fraction was collected and concentrated under reduced pressure. The concentrated solution was further subjected to column chromatography using silica gel (150 ml; Fuji-Davison, BW-300) and a solvent system of chloroform/methanol (85:15 v/v). The blue fraction was collected and concentrated under reduced pressure to obtain 248 mg of Compound 14 in the form of dark blue powders with a yield of 41%. The product showed a molar ratio of mitomycin type substance of >99%. The physico-chemical characteristics of this compound were as follows:

SIMS: m/z 610(M+3)$^+$ (Molecular formula $C_{24}H_{29}N_7O_8S_2$; M.W. 607.7).

$^1$H-NMR (400 MHz):(Py-d$_5$) δ 2.11 (3H, s), 2.75 (1H, dd, J=4.4, 1.8 Hz), 2.97 (2H, t, J=6.8 Hz), 3.14 (1H, d, J=4.4 Hz) 3.14 (2H, t, J=6.7 Hz), 3.23 (3H, s), 3.61 (1H, dd, J=12.7, 1.8 Hz), 3.92 (2H, q, J=6.8 Hz), 3.94 (2H, q, J=6.7 Hz), 4.00 (1H, dd, J=11.1, 4.2 Hz), 4.52 (1H, d, J=12.7 Hz), 5.04 (1H, dd, J=11.1, 10.4 Hz), 5.38 (1H, dd, J=10.4, 4.2 Hz), 6.61 (1H, s), 7.25 (1H, t, J=6.6 Hz), 7.63 (2H, br.), 10.07 (1H, t, J=5.5 Hz), 13.29 (2H, br.).

IR: (KBr) cm$^{-1}$ 3450, 3405, 3270, 1715, 1635, 1560, 1540, 1510, 1445, 1420, 1325, 1060.

EXAMPLES 15-16

Compounds 15 and 16 were prepared in a similar manner to that described in Example 14, which exhibited $^1$H-NMR and IR data as shown in Table 7 hereinafter. It was noted that the molar molar ratio of the mitomycin-type contained in the products was >99%.

EXAMPLE 17

503 mg of 7-N-[2-(2-pyridyl)dithioethyl]mitomycin D (disclosed in EP 0116208A1 and Japanese laid open Patent Application 175493/84) was dissolved in acetonitrile (10 ml). To this solution were added dropwise a solution of acetonitrile (10 ml) containing 2-acetylthioethylamine hydrochloride (148 mg) and triethylamine (150 μl) while stirring and ice-cooling. After this, the reaction solution was passed through a column packed with silica gel (200 ml. Fugi-Davison BW-300). Elution was effected by using a solvent system of chloroform/methanol (9:1 v/v) to give a blue fraction which showed a RF value of 0.22 by TLC using silica gel (Merck 60F$_{254}$ Art 5719) and a solvent system of chloroform/methanol (9:1:v/v). The solvent was removed from the blue fraction by evaporation under reduced pressure. The residue was dissolved in chloroform. The solution was dropwise added to n-hexane to obtain precipitates which were filtered to remove the solvent, resulting in 360 mg of Compound 17 in the form of grayish blue powders with a yield of 70%. The physico-chemical characteristics of this compound were as follows:

SIMS: m/z 513(M+2)$^+$, 514(M+3)$^+$, (Molecular formula $C_{21}H_{29}N_5O_6S_2$; M.W 511.6).

$^1$H-NMR (400 MHz): (Py-d$_5$) δ 2.07 (6H, s), 2.13 (3H, s), 2.24 (1H, dd, J=4.1, 1.9 Hz), 2.47 (1H, d, J=4.7 Hz), 2.90 (2H, t, J=6.8 Hz), 3.02 (2H, t, J=6.6 Hz), 3.68 (1H, dd, J=12.9, 1.9 Hz), 3.77 (2H, q, J=6.3 Hz), 3.85 (2H, q, J=6.7 Hz), 4.22 (1H, dd, J=10.0, 3.4 Hz), 4.43 (1H, d, J=12.9 Hz), 5.21 (1H, t, J=10.3 Hz), 5.47 (1H, dd, J=10.6, 3.4 Hz), 7.23 (1H, t, J=6.5 Hz), ~7.5 (2H, bs.s), 8.34 (1H, br. s), 8.77 (1H, br. t).

IR: (KBr) cm¹ 3350, 1716, 1649, 1557, 1548, 1511, 1320.

EXAMPLES 18-20

Table 8 described hereinafter indicates SIMS, $^1$H-NMR and IR of Compounds 18-20 prepared in a similar manner to that described in Example 17. The molar ratio of mitomycin-type substance contained in the isolated Compound 19 was >99%.

EXAMPLE 21

N-succinimidyl 3-(2-pyridyldithio)propionate (180 mg) was dissolved in methanol (4.5 ml), to which was added 1 ml of a methanol solution of ammonia (5% v/v). The mixture was stirred at 0° C. for 30 minutes, followed by concentration to 1 ml under reduced pressure. As a result, 3-(2-pyridyldithio)propanamide [disclosed in Japanese laid open Patent Application 57595/86 and CA105(19)173000q] was formed in the reaction solution. To this solution were added triethylamine (80 ml) and cysteamine hydrochloride (65 mg). The solution was stirred at room temperature for 10 minutes. Then, mitomycin A (50 mg) was added to the reaction solution, followed by stirring at room temperature for 2 hours. After addition of water (10 ml), the solution was extracted with chloroform (50 ml). The chloroform solution was dried with sodium sulfate, and the solvent was removed under reduced pressure. The material was chromatographed by the use of silica gel (10 ml; Wako-C200) and a solvent system of chloroform/methanol (9:1 v/v). The resultant blue fractions were collected combined, and concentrated. The concentrated fraction was dissolved in acetone and was dropwise added to cyclohexane to give precipitates. The precipitates were dryed under reduced pressure to obtain yellowish green powders of Compound 21 (15 mg) with a yield of 21%. The molar ratio of mitomycin-type substance contained in the produce was >99%.

The physico-chemical characteristics of the isolated compound were as follows:

SIMS: m/z 499 (M+2)+, $^1$H-NMR (400 MHz): (Py-d$_5$) δ 2.10 (1H, br), 2.12 (3H,s) 2.74 (1H, br. s), 2.90 (b 2H, t, J=7.4 Hz), 2.95 (2H, t, J=6.9 Hz), 3.13 (1H, br. s), 3.22 (3H, s), 3.26 (2H, t, J=7.1 Hz), 3.59 (1H, br. d, J=12.6 Hz), 3.91 (2H, q, J=6.6 Hz), 3.99 (1H, dd, J=11.3, 4.4 Hz), 4.52 (1H, d, J=12.6 Hz), 5.05 (1H, br. dd, J=11.3, 10.3 Hz), 5.38 (1H, dd, J=10.3 4.4 Hz), 7.20 (1H, br.), 7.78 (2H, br.), 8.33 (2H, br.).

IR: (KBr) cm$^{-1}$ 3400, 3280, 2930, 1720, 1700, 1670, 1630, 1560, 1505, 1445, 1315, 1200, 1050, 850, 760.

EXAMPLES 22-25

Compounds 22-25 were prepared in a similar manner to that described in Example 1. Their SIMS, $^1$H-NMR and IR data are shown in Table 9 hereinafter.

Compounds 22 and 23 were isolated as mixtures of mitomycin-type substance and albomitomycin-type substance at the following molar ratios:

| Compound | Mitomycin-type | Albomitomycin-type |
|---|---|---|
| 22 | 85 | 15 |
| 23 | 87 | 13 |

EXAMPLE 26

β-estradiol 3-benzoate (376 mg) and thioglycolic acid (69.4 μl) were added to dry toluene (5 ml) and heated for 1.5 hours under reflux in argon stream to give a solution A containing Compound III. 7-N-[2-(2-pyridyl)dithioethyl]mitomycin C (252 mg) was dissolved in a mixture of chloroform/methanol (4 ml, 1:1 v/v). To the mixture, triethylamine (0.2 ml) was added. Then, to this solution was dropwise added said solution A, followed by stirring for 5 minutes. After addition of water (10 ml), the solution was extracted with chloroform (100 ml).

The chloroform solution was dried using sodium sulfate. The solution was removed by evaporation under reduced pressure. The solution was chromatographed by the use of a column packed with silica gel (50 ml, Wako-C200) and a solvent system of chloroform/acetone/methanol (70:25:5 v/v). The eluate was concentrated under reduced pressure and was dissolved in a small amount of chloroform. The chloroform solution was dropwise added to n-hexane to give precipitates. The precipitates were dried under reduced pressure to obtain Compound 26 in the form of blueish purple powders (260 mg) with a yield of 62%. The molar ratio of mitomycin-type substance present in the product was >99%.

The physico-chemical characteristics of Compound 26 were as follows:

SIMS: m/z 844 (M+2)+, $^1$H-NMR (400 MHz):(CDCl$_3$) δ 0.87 (3H, s), 2.03 (3H,s), 2.81 (1H, bs.(, 2.96 (2H, t, J=6.6Hz), 3.20 (3H, s), 3.51 (1H, br. d, J=12.9 Hz), 3.51 (2H, AB, J=14.7 Hz), 3.60 (1H, dd, J=10.5, 4.3 Hz), 3.90 (2H, br. q, J=6.5 Hz), 4.27 (1H, d, J=12.9 Hz), 4.49 (1H, br. t, J=10.7 Hz), 4.70 (1H, dd, J=10.7, 4.3 Hz), 4.76 (1H, dd, J=8.9, 7.9 Hz), 4.82 (2H, br. s), 6.49 (1H, t, J=6.3 Hz), 6.92 (1H, br.d, J=2.5 Hz), 6.97 (1H, dd, J=8.4, 2.5 Hz), 7.33 (1H, br, d, J=8.4 Hz), 7.50 (2H, t, J=7.7 Hz), 7.63 (1H, tt, J=7.4, 1.3 Hz), 8.19 (2H, d, J=8.3 Hz).

IR: (KBr) cm$^{-1}$ 3420, 3290, 2925, 1720, 1710, 1555, 1505, 1450, 1325, 1265, 1215, 1060.

EXAMPLES 27-32

The SIMS, $^1$H-NMR and IR data of Compounds 27-32 are shown in Table 10 hereinafter.

Compounds 27-30 were prepared in a similar manner to that described in Example 26, while Compound 31-32 were prepared in a similar manner to that described in Example 21.

EXAMPLE 33

200 mg of 7N-[2-(2-hydroxyethyl)dithio]ethyl]mitomycin C (disclosed in Japanese laid open Patent Application 175493/84) was dissolved in dry tetrahydrofuran (6 ml), to which was then added triphenyl phosphine (257 mg) under nitrogen stream. To this solution was added diisopropyl azodicarboxylate (193 μl) at 0° C., followed by addition of thioacetic acid (70 μl) while stirring for 10 minutes. After addition of water (20 ml), the reaction solution was extracted with chloroform (100 ml). The chloroform solution was dried with sodium sulfate, and then the solvent was removed by evaporation under reduced pressure. The residual material was chromatographed by the use of a column packed with silica gel (50 ml; Wako C200) and a solvent system of chloroform/methanol (98:2 v/v). The resultant blue fractions were collected, concentrated and dissolved in a small amount of acetone. The material was then dropwise added to cyclohexane to obtain precipitates which were filtered to remove the solvent. There was obtained grayish blue Compound 33 (49 mg) with a yield of 22%. The isolated compound showed a molar ratio of mitomycin-type substance of >99%.

The physico-chemical characteristics of this compound were as follows:

SIMS: m/z 530 (M+2)$^+$.

$^1$H-NMR (400 MHz):(Py-d$_5$) δ 2.10 (1H, br.), 2.14 (3H,s), 2.27 (3H, s), 2.75 (1H, br.), 2.95 (1H, t, J=7.4 Hz), 2.99 (2H, t, J=6.6 Hz), 3.15 (1H, br), 3.22 (3H, s), 3.31 (2H, t, J=7.4 Hz), 3.59 (1H, br. d, J=12.3 Hz), 3.93 (2H, q, J=6.6 Hz), 4.00 (16 H, dd, J=11.1, 4.2 Hz), 4.52 (1H, d, J=12.8 Hz), 5.08 (1H, br, dd, J=11.0, 10.8 Hz), 5.38 (1H, dd, J=10.7, 4.2 Hz), 7.26 (1H, t, J=6.6 Hz), 7.60 (2H, br.).

IR: (KBr) cm$^{-1}$ 3450, 3280, 2930, 1715, 1700, 1630, 1560, 1510, 1440, 1320, 1060, 935, 855.

EXAMPLES 34-35

The SIMS, $^1$H-NMR and IR data of Compounds 34 and 35 prepared in a similar manner to that described in Example 33 are shown in Table 11 hereinafter. The molar ratio of mitomycin-type substance in Compound 35 was >99%.

EXAMPLE 36

Compound 36 having the following physico-chemical characteristics was obtained in a similar manner to that described in Example 1. the molar ratio of mitomycin-type substance found in Compound 36 was 89:11.

SIMS: m/z 579 (M+2)$^+$.

$^1$H-NMR (400 MHz):(D$_2$O) δ 1.93*(s), 2.01 (3H, s), 3.02 (2H, t, J=6.2 Hz), 3.04 (2H, m), 3.06 (1H, dd, J=4.6, 2.1 Hz), 3.09 (1H, d, J=4.6 Hz), 3.27 (3H, s), 3.44* (s), 3.62 (1H, dd, J=13.3, 2.1 Hz), 3.65 (1H, dd, J=10.7, 4.6 Hz), 4.03 (2H, t, J=6.4 Hz), 4.18 (1H, d, J=13.3 Hz), 4.26 (1H, t, J=10.7 Hz), 4.59 (1H, dd, J=10.7, 4.6 Hz).

IR: (KBr) cm$^{-1}$ 3450, 1705, 1630, 1550, 1510, 1460, 1330, 1210, 1180, 1045.

EXAMPLE 37

7-N-[2-(2-pyridyl)dithioethyl] mitomycin C (200 mg) (disclosed in EP 0116208A and Japanese laid open Patent Application 185493/84) was dissolved in methanol (50 ml). To this solution was added 5-mercaptomethyl uracil (62 mg) while stirring for 30 minutes at room temperature. After removal of the solvent by evaporation under reduced pressure, the reaction solution as chromatographed using a column packed with silica gel (100 ml; Wako C200) and a solvent system of chloroform/methanol (9:1~4:1 v/v). The eluted blue fractions were collected and combined. The solvent was removed by evaporation under reduced pressure to obtain Compound 37 (155 mg) with a yield of 70%. It was noted that Compound 37 was isolated as a compound containing mitomycin-type substance at a molar ratio of >99%.

The physico-chemical characteristics of this compound were as follows:

SIMS: m/z 551 (M+2)$^+$.

$^1$H-NMR (100 MHz):(Py-d$_5$) δ 2.05 (1H, br.), 2.76 (1H, br.), 3.01 (2H, t, J=6.6 Hz), 3.11 (1H, br.), 3.22 (3H, s), 3.70 (1H, br. d, J=12.7 Hz), 5.02 (1H, br.), 5.38 (1H, dd, J=10.5, 4.4 Hz), 7.25 (1H, br. t, J=7.3 Hz), 7.64 (2H, br.), 7.82 (1H, s).

IR: (KBr) cm$^{-1}$ 3440, 3280, 2950, 1710, 1700, 1680, 1555, 1505, 1455, 1330, 1210, 1060.

EXAMPLES 38-40

Compounds 38-40 were obtained in a similar manner to that described in Example 37. Their SIMS, $^1$H-NMR and IR data are shown in Table 12 hereinafter. The molar ratio of mitomycin-type substance contained in Compound 39 was >99%.

EXAMPLE 41

Synthesis of Compound 6 (Another Method)

Compound C (600 mg) obtained by he method described in Reference 3 hereinafter was dissolved in dichloromethane (28 ml). To this solution was added anisole (2.8 ml). After addition of trifluoroacetic acid (28 ml) and trifluoromethane sulfonic acid (1.68 ml) at a temperature of 0° C., the mixture was stirred for 30 minutes, followed by further stirring at room temperature for 4 hours. To the reaction solution was added water (50 ml). Then the solution was extracted three times with ether (each 50 ml). The aqueous layer was concentrated under reduced pressure. To the concentrated solution was added a phosphate buffered-solution (M/10; pH 7.5; 30 ml), followed by addition of a small amount of an aqueous solution of saturated sodium bicarbonate to give a pH of 5.5. The reaction solution was applied to a column packed with Diaion SP-207 (100 ml; commercial product of Mitsubishi Kasei Kogyo K.K., Japan). After washing the column with water (200 ml), elution was effected using a solvent system of water/methanol (300 ml; 5:95~10:90 v/v). The resultant fractions were collected, combined and concentrated under reduced pressure. The concentrate was freeze-dried to give crude powders of N-(β-L-aspartyl) cysteamine (130 mg) with a yield of 60%. The powders were not purified further but were used for the reaction with 7-N-[2-(2-pyridyl)dithioethyl]mitomycin C (340 mg). The reaction was effected in a similar manner to that described in Example 1 to obtain 168 mg of Compound 6 with a yield of 42%.

EXAMPLE 42

Injection Agent

A compound prepared by the method of Example 1 viz. Compound 1 (20 g) and purified mannitol (40 g) were dissolved in a sterilized water for injection and made up to 20 liter in total. The solution was divided into fractions (each 5 ml). Each fraction was put into a brown vial and freeze-dried in conventional manner to obtain a freeze-dried injection agent (5 ml per vial).

EXAMPLE 43

Tablet

Lactose (40 g), calcium carbonate (1200 g) and calcium carboxymethylcellulose (300 g) were mixed together. To this mixture was added (500 g) of hydroxypropyl methylcellulose (16% aqueous solution as bonding agent). The materials were well mixed together, granulated and dried. Before well mixing, 10 g of Compound 17 was added thereto. After addition of of magnesium stearate (10 g), the mixture was treated by using a tablet machine (Kikusui K.K., Japan; Type RT 15; the diameter of the punches being 8 mm) to prepare tablets (each 200 mg, containing 1 mg of Compound 17).

REFERENCE 1

Synthesis of Compound "a"

859 mg of N,N'-bis[N-carbobenzyloxy-γ-(α-benzyl-L-glutamyl]cystamine (disclosed in Japanese laid open Patent Application 4121/76) was dissolved in dichloromethane (25 ml). To this solution was added anisole (2.5 ml) while cooling with ice, followed by addition of trifluoromethanesulfonic acid (1.5 ml). The mixture was stirred for 30 minutes while cooling with ice, followed by further stirring at room temperature for one hour. The reaction solution was concentrated under reduced pressure. Then decantation was effected twice by using ether (each 30 ml). The residue was dissolved in a buffer solution (50 ml) of M/15 $Na_2HPO_4$-M/15 $K_2HPO_4$ (1:1 v/v) and applied to a column packed with Diaion SP-207 (50 ml; commercial product of Mitsubishi Kasei Kogyo K.K., Japan). After washing the column with water (150 ml), a solvent system of water/methanol (100 ml; 4:1 v/v) was passed through the column. The resultant fractions were collected, combined, concentrated under reduced pressure, and freeze-dried to obtain N,N'-bis(γ-L-glutamyl)cystamine viz. Compound "a" (402 mg) with a yield of 98%.

The physico-chemical characteristics of the resultant compound were as follows:

SIMS: m/z 411(M+1)+, (Molecular formula $C_{14}H_{26}N_4O_6S_2$; M.W. 410.5).

1H-NMR (400 MHz):($D_2O$) δ 2.18 (4H, m, 2.45 (4H, m), 2.84 (4H, m), 3.51 (4H, m.), 3.67 (2H, m).

IR: (KBr) $cm^{-1}$ 3450, 3100, 2940, 1680, 1638, 1200, 1136.

Optical rotation: $[\alpha]_D^c$ +11.5° (c 0.47, $H_2O$).

REFERENCE 2

Synthesis of Compound "b"

Compound "a" (205 mg) described in Reference 1 was dissolved in water/ethanol (20 ml; 3:1 v/v). After adding ethanethiol (3 ml), the mixture was stirred at room temperature for 3 days. The solvent was removed by evaporation under reduced pressure. The reside was applied to a column packed with Diaion SP-207 (25 ml). Water (75 ml) was passed through the column. Then elution was effected by using a solvent system of water/methanol (50 ml; 9:1 v/v). The eluted fractions were collected, combined and concentrated under reduced pressure, followed by freeze-drying to obtain γ-L-glutamylcysteamine (Compound "b") (190 mg) with a yield of 92%.

This compound showed the following physico-chemical characteristics:

SIMS: m/z 207(M+1)+, (Molecular formula $C_7H_{14}N_2O_3S$; M.W. 206.3).

1H-NMR (400 MHz):($D_2O$) δ 2.18(4H, m), 2.46(4H, m), 2.62 (4H, m), 3.34 (4H,m.), 3.72 (2H, m).

IR: (KBr) $cm^{-1}$ 3400, 3100, 2940, 1640, 1530, 1410, 1205, 1135.

Optical rotation: $[\alpha]_D^c$ +11.2° (C 0.99, $H_2O$).

REFERENCE 3

Synthesis of Compound "c"

N-carbobenzoxy-α-benzyl-L-aspartic acid (1.617 g; commercially available from Kokusan Kagaku K.K., Japan, 2509181) was dissolved in dichloromethane (20 ml). To this solution were added N-hydroxy-succinimide (522 mg) and dicyclohexylcarbodiimide (933 mg). The mixture was stirred at a temperature of 0° C. for 2 hours and further stirred at room temperature for 18 hours. Then, to the reaction solution were added 2-[(p-methoxybenzyl)thio]ethylamine hydrochloride (1 g) and triethylamine (623 μl). The mixture was stirred at room temperature for 2 hours. The resultant precipitates were separated by filtration. After addition of an aqueous solution of 10% citric acid (30 ml), the reaction mixture was extracted with ethyl acetate (150 ml). The extracted solution was washed with 5% sodium bicarbonate solution (30 ml) and a saturated solution of sodium chloride (30 ml) and was then dried by using sodium sulfate. After removing the solvent by evaporation under reduced pressure, the residue was subjected to silica gel chromatography using a column packed with silica gel (150 g; Wako Gel C200). Elution was effected by a solvent system of chloroform/methanol (99:1 v/v) to obtain N-[N-carbobenzoxy-β-(α-benzyl)-L-aspartyl]-S-(p-methoxybenzyl)cysteamine viz. Compound "c" (1.929 g) with a yield of 80%.

The physico-chemical characteristics of the product were as follows:

SIMS: m/z 537(M+1)+, (Molecular formula $C_{29}H_{32}N_2O_6S$; MW 536.6).

1H-NMR (400 MHz):($CDCl_3$) δ 2.50(2H, t, J=7 Hz), 2.78 (2H, AB, J=16.4 Hz), 3.33 (2H, q, J=7.0 Hz), 3.64 (2H, s), 3.79 (3H, s.), 4.63 (1H, dt, J=8.5, 5.4 Hz), 5.12 (2H, s), 5.19 (2H, s), 5.83 (1H, br), 6.07 (1H, br. d), 6.88 (2H, d, J=9.0 Hz), 7.24 (2H, d, J=9.0 Hz), 7.36 (10H, s).

IR:(KBr) $cm^{-1}$ 3300, 2900, 1735, 1695, 1635, 1535, 1510, 1285, 1250, 1065, 745, 695.

REFERENCE 4

The following compounds were obtained in a similar manner to that described in Reference 3 except the use of the following compounds instead of 2-[(p-methoxybenzyl)thio]ethylamine:

homocystamine (Merck Index, 10th Edit., 2771, 1983) for the preparation of Compound "d";

bishomocystamine (disclosed in Japanese Patent Publication 54314/81) for the preparation of Compound "e"; and cystamine for the preparation of Compounds "f" and "g".

In the reactions, it was necessary, in general, to double the molar amount of the protected amino acid disclosed in Reference 3. Pyroglutamic acid was used for the preparation of Compound "f".

The SIMS, IR and 1H-NMR data of the resultant compounds are indicated in Table 13 hereinafter.

Compound "d": N,N'-bis[N-carbobenzoxy-γ-(α-benzyl)-L-glutamyl]homocystamine

Compound "e": N,N'-bis[N-carbobenzoxy-γ-(α-benzyl)-L-glutamyl]bishomocystamine

Compound "f": N,N'-bis(L-pyroglutamyl)cystamine

Compound "g": N,N'-bis(N-t-butyloxycarbonyl-L-prolyl)cystamine

By the similar methods to those described in References 1 and 2, the desired mercaptan III was obtained by using Compounds "d" and "e" respectively. In a similar manner to that described in Reference 2, the desired mercapatan III was obtained from Compound "f". Compound "g" was treated with trifluoroacetic acid and then treated in a similar manner to that described in Reference 2 to obtain the desired mercaptan III.

REFERENCE 5

The following compounds were obtained in a similar manner to that described in Reference 3. Their SIMS, IR and $^1$H-NMR data are shown in Table 14 hereinafter:

Compound "h": N-[N-t-butyloxycarbonyl-α-(β-benzyl)-L-aspartyl]-S-(p-methoxybenzyl)cysteamine
Compound "i": N-[N-t-butyloxycarbonyl-α-(γ-benzyl)-L-glutamyl]-S-(p-methoxybenzyl)cysteamine
Compound "j": N-[N-carbobenzoxy-α-(γ-benzyl)-L-glutamyl]-S-(p-methoxybenzyl)cysteamine
Compound "k": N-[N-carbobenzoxy-γ-(α-benzyl)-D-glutamyl]-S-(p-methoxybenzyl)cysteamine The desired mercaptan was obtained in a similar manner to that described in Reference 1 by using these compounds.

REFERENCE 6

From orotic acid and 2-(2-pyridyldithio)ethylaminedihydrochloride (disclosed in Japanese laid open Patent Application 136261/80) was obtained N-2-(2-pyridyldithio)ethyl-6-uracylamide viz. Compound "1". This compound was used as raw material for the preparation of the compound disclosed in Example 14 without further purification.

The physico-chemical characteristics of crude Compound "1" were as follows:

SIMS: (m/z) 325(M+1)$^+$.

$^1$H-NMR (90 MHz):(Py-d$_5$) δ 3.11(2H, t.), 3.79 (2H, q), 6.43 (1H, s), 6.978 (1H, m), 7.54 (2H, m), 8.46 (1H, m), 9.87 (1H, m).

In a similar manner to that described above, there was obtained Compound "m" viz. N-2-(2-pyridyldithio)ethylretinamide which was unstable, while d-6-[2-(2-pyridyldithio)ethylcarbamoyl)]propanoyl]tocopherol viz.

Compound "n" was relatively stable. Although SIMS of Compound "n" were not observed, its $^1$H-NMR and IR data were as follows:

$^1$H-NMR (90 MHz):(CDCl$_3$) δ 0.88 (12H, d), 1.00~1.64 (21H, m), 1.76 (2H, t), 1.94 (3H,s), 1.98 (3H,s), 2.02 (3H,s), 2.07 (3H,s), 2.62 (4H, m), 2.95 (4H, q), 3.56 (2H, q), 7.15 (2H, m), 7.50 (2H, m), 8.48 (1H, m).

IR: (KBr) cm$^{-1}$ 3240, 2930, 1745, 1665, 1455, 1415, 1150.

REFERENCE 7

To 3-mercaptopropionic acid (8.71 ml) was dropwise added an aqueous solution of hydrogen peroxide (9.72 g; 35% w/w) in 30 minutes with stirring while cooling with ice. The mixture was further stirred at 0° C. for one hour. The resultant white precipitates were dried under reduced pressure for 2 days by using phosphorous pentoxide to give crude powders of 3,3'-dithiopropionic acid (10.6 g). The resultant crude powders (4.27 g) were dissolved in dioxane (70 ml). To the solution were added N-hydroxysuccinimide (5.16 g) and dicyclohexylcarbodiimide (10.52 g). The mixture was stirred at room temperature for 5 hours. The resultant precipitates were separated by filtration. Ethyl acetate (300 ml) was added to the mother liquor which was then washed with an aqueous solution of 5% sodium bicarbonate (50 ml), followed by further washing with saturated solution of sodium chloride. After drying with sodium sulfate, the reaction solution was evaporated under reduced pressure to remove the solvent and was then chromatographed using a column packed with silica gel (Wako C200)) and a solvent system of chloroform/methanol (99:1 v/v). The eluted fractions were collected, combined and concentrated to obtain bis]N-hydroxysuccinimide]ester of 3,3'-dithiopropionic acid (Compound "B") (5.57 g) in the form of white powders with a yield of 67% on the basis of 3-mercaptopropionic acid. The physico-chemical characteristics of this compound were as follows:

SIMS: m/z 405 (M+1)$^1$.

$^1$H-NMR (90 MHz):(CDCl$_3$) δ 2.82 (8H, s), 3.06 (8H,s). Compound "B" and benzyl N$^5$-carbobenzoxy-L-ornithinate hydrochloride [disclosed in Annalen der Chemie, 676, 232 (1964)] were treated in a similar manner to that described in Reference 3 to prepare Compound "o" viz. dibenzyl N',N''-(2,2'-dithiodiethylene-1,1'-dicarbonyl)bis(N$^6$-benzyloxycarbonyl-L-orthinate).

Compound "B" and benzyl N$^6$-carbobenzoxy-L-lysinate p-toluene sulfonate [disclosed in Bulletin of the Chemical Society of Japan, 40, 1945 (1967)] were treated in a similar manner to that described above to obtain Compound "p" viz. dibenzyl N',N''-(2,2'-dithiodiethylene-1,1'-dicarbonyl)-bis(N$^6$-benzyloxycarbonyl-L-lysinate). The physico-chemical characteristics of Compounds "o" and "p" are shown in Table 15 described hereinafter.

REFERENCE 8

Compound "o" was treated in a similar manner to that described in Reference 1 to obtain N',N''-(2,2'-dithiodiethylene-1,1'-dicarbonyl)-bis (L-ornithine) viz. Compound "q". Separately, in a similar manner to that described in Reference 1, N',N''(2,2'-dithiodiethylene-1,1'-dicarbonyl)-bs(L-lysine) viz. Compound "r" was obtained from Compound "p". From these dimers, the corresponding monomers of mercaptan were obtained in a similar manner to that described in Reference 2. The physico-chemical characteristics of Compounds "q" and "r" are shown in Table 16 hereinafter.

INDUSTRIAL APPLICABILITY OF THE INVENTION

Mitomycin derivatives according to the present invention may be used as anti-tumour agents with respect to their anti-tumour activities which are, in general, higher than the anti-tumour activity of mitomycin C as well as to their lower toxicity and they have high solubility in water or lipid.

TABLE 6

| No. | SIMS (m/z) | IR(KBr) cm$^{-1}$ | $^1$H-NMR (D$_2$O) δ (400MHz) |
|---|---|---|---|
| 3 | 599(M+1)$^+$ 600(M+2)$^+$ | 3420, 1705, 1685, 1640, 1510, 1400, 1330, 1250, 1155, 1065, 1030 | 1.92*(s), 1.94(3H,s), 2.13 (2H,m), 2.42(2H,m), 2.84(2H, t,J=6.3Hz), 2.97(2H,t,J=6.3 Hz), 3.03(1H,br.), 3.07(1H, br.), 3.29(3H,s), 3.43*(s), 3.51(2H,t,J=6.3Hz), 3.61 (1H,dd,J=10.7, 4.6Hz), 3.62 (1H,br.), 3.76(1H,t,J=6.1Hz) 3.97(2H,t,J=6.3Hz), 4.16(1H, br.d,J=12.4Hz), 4.24(1H,br. t,J=10.7Hz), 4.58(1H,dd,J= 10.7, 4.6Hz) |
| 4 | 613(M+1)$^+$ 614(M+2)$^+$ | 3400, 3300, 1715, 1635, 1560, 1515, 1450, 1325, 1060 | 1.88(2H,quintet,J=6.9Hz), 1.93*(s), 2.00(3H,s), 2.11 (2H,m), 2.40(2H,m), 2.73 (2H,t,J=7.1Hz), 3.00(2H,t,J= 6.3Hz), 3.06(1H,br.), 3.09 |

TABLE 6-continued

| No. | SIMS (m/z) | IR(KBr) cm$^{-1}$ | $^1$H-NMR (D$_2$O) δ (400MHz) |
|---|---|---|---|
| | | | (1H,br.), 3.26(2H,t,J=6.8Hz), 3.28(3H,s), 3.44*(s), 3.64 (2H,m), 3.73(1H,t,J=6.1Hz), 4.02(2H,t,J=6.2Hz), 4.18(1H, br.d,J=12.4Hz), 4.25(1H,br.t, J=10.8Hz), 4.32*(dd), 4.41* (dd), 4.59(1H,dd,J=10.8, 4.6 Hz) |
| 5 | 627(M+1)$^+$ 628(M+2)$^+$ | 3400, 3300, 1720, 1700, 1685, 1655, 1650, 1640, 1565, 1540, 1520, 1510, 1505, 1450, 1330, 1060 | 1.56(2H,m), 1.67(2H,m), 1.93*(s), 1.99(3H,s), 2.13(2H,m), 2.41(2H,m), 2.71 (2H,t,J=6.8Hz), 2.97(2H,t, J=6.2Hz), 3.03(1H,br.), 3.06 (1H,br.), 3.18(2H,t,J=6.8Hz), 3.28(3H,s), 3.44*(s), 3.62 (1H,dd,J=10.7, 4.4Hz), 3.64 (1H,br.), 3.76(1H,t,J=6.1Hz), 3.98(2H,t,J=6.2Hz), 4.18 (1H,br.d,J=13.4Hz), 4.24 (1H,br.t,J=10.7Hz), 4.58 (1H,dd,J=10.7, 4.4Hz) |
| 6 | 585(M+1)$^+$ 586(M+2)$^+$ | 3300, 1715, 1705, 1655, 1630, 1560, 1550, 1515, 1510, 1450, 1330, 1215, 1060 | 1.93*(s), 1.99(3H,s), 2.81 (1H,dd,J=16.6, 8.1Hz), 2.85 (2H,t,J=6.3Hz), 2.93(1H,dd, J=16.6, 4.4Hz), 2.99(2H,t,J= 6.3Hz), 3.03(1H,br.), 3.06(1H, br.), 3.29(3H,s), 3.44*(s), 3.52(2H,m), 3.63(1H,dd,J= 10.7, 4.4Hz), 3.65(1H,br.), 4.00(2H,t,J=6.3Hz), 4.01(1H, dd,J=8.1, 4.4Hz), 4.18(1H, br.d,J=13.2Hz), 4.24(1H,br. t,J=10.7Hz), 4.59(1H,dd,J= 10.7, 4.4Hz) |
| 7 | 585(M+1)$^+$ 586(M+2)$^+$ | 3400, 3260, 1705, 1690, 1550, 1505, 1450, 1330, 1220, 1060 | 1.93*(s), 1.99(3H,s), 2.66(1H, dd,J=17.1, 8.3Hz), 2.77(1H,dd, J=17.1, 5.1Hz), 2.85(2H,t,J= 6.3Hz), 3.00(2H,t,J=6.3Hz), 3.03(1H,br.), 3.06(1H,br.), 3.28 (3H,s), 3.44*(s), 3.43(1H,dt,J= 14.2, 6.3Hz), 3.61(1H,dt,J= 14.2, 6.3Hz), 3.64(1H,dt,J= 10.7, 4.6Hz), 3.64(1H,br.), 4.00(2H,t,J=6.3Hz), 4.11(1H, dd,J=8.3, 5.1Hz), 4.13(1H,br.d, J=13.4Hz), 4.24(1H,br.t,J= 10.7Hz), 4.59(1H,dd,J=10.7, 4.6Hz) |
| 8 | 582(M+2)$^+$ | 3270, 1720, 1700, 1690, 1670, 1645, 1545, 1505, 1450, 1320, 1055 | 1.95*(s), 2.01(3H,s), 2.11(1H, m), 2.43(1H,dd of ABd,J=17.4, 9.9, 6.0Hz), 2.47(1H,dd of ABd, J=17.4, 9.5, 6.3Hz), 2.57(1H, m), 2.89(2H,t,J=6.3Hz), 3.02 (2H,t,J=6.3Hz), 3.07(1H,br.), 3.11(1H,br.), 3.31(3H,s), 3.46*(s), 3.58(2H,t,J=6.3Hz), 3.65(1H,br.d), 3.66(1H,dd,J= 10.7, 4.5Hz), 4.02(2H,t,J= 6.3Hz), 4.20(1H,br.d,J=13.4 Hz), 4.27(1H,br.t,J=10.7Hz), 4.33(1H,dd,J=9.0, 5.1Hz), 4.61(1H,dd,J=10.7, 4.5Hz) |
| 9 | 599(M+1)$^+$ 600(M+2)$^+$ | 3440, 3290, 1710, 1700, 1695, 1690, 1625, 1560, 1545, 1510, 1460, 1325, 1060 | 1.93*(s), 2.00(3H,s), 2.11(2H, m), 4.25(1H,t,J=10.8Hz), 4.59 (1H,m), 2.37(2H,m), 2.88(2H, m), 3.01(2H,t,J=6.2Hz), 3.03 (1H,dd,J=4.5, 1.8Hz), 3.07(1H, d,J=4.5Hz), 3.29(3H,s), 3.44* (s), 3.53(1H,dt,J=14.0, 6.2Hz), 3.65(1H,dd,J=10.8, 4.5Hz), 3.66(1H,dt,J=14.0, 6.8Hz), 3.66(1H,br.d,J=13.3Hz), 4.01(2H,t,J=5.8Hz), 4.01(1H,t, J=6.5Hz), 4.19(1H,d,J=13.3 Hz), 4.25(1H,t,J=10.8Hz), 4.59 (1H,dd,J=10.8, 4.5Hz) |
| 10 | 586(M+2)$^+$ 587(M+3)$^+$ | 3400, 3300, 1715, 1700, 1685, 1655, 1640, 1560, | 1.99(3H,s), 2.31(3H,s), 2.61 (1H,d,J=4.8Hz), 2.71(1H,dd,J= 4.8, 2.1Hz), 2.80(1H,dd,J= 16.6, 7.9Hz), 2.85(2H,t,J=6.5 |
| | | 1510, 1475, 1330 | Hz), 2.92(1H,dd,J=16.6, 4.3 Hz), 3.01(2H,t,J=6.3Hz), 3.51 (1H,t of AB,J=13.9, 6.3Hz), 3.54(1H,t of AB,J=13.9, 6.3 Hz), 3.66(1H,dd,J=13.6, 2.1 Hz), 3.74(1H,dd,J=9.2, 3.6Hz), 4.00(1H,dd,J=7.9, 4.3Hz), 4.04(2H,br.t,J=6.1Hz), 4.09 (1H,d,J=13.6Hz), 4.41(1H,dd, J=10.9, 9.2Hz), 4.69(1H,dd,J= 10.9, 3.6Hz) |
| 11 | 600(M+1)$^+$ 601(M+2)$^+$ | 3430, 1735, 1700, 1640, 1545, 1520, 1450, 1340, 1120, 1060, 850 | 1.98(3H,s), 2.13(2H,m), 2.30 (3H,s), 2.41(2H,m), 2.60(1H,d, J=4.8Hz), 2.69(1H,dd,J=4.9, 2.0Hz), 2.84(2H,t,J=6.1Hz), 2.99(2H,t,J=6.3Hz), 3.51(2H,t, J=6.1Hz), 3.64(1H,dd,J=13.7, 2.0Hz), 3.73(1H,dd,J=9.5, 3.7 Hz), 3.75(1H,t,J=6.1Hz), 4.02 (2H,t,J=6.3Hz), 4.08(1H,d,J= 13.4Hz), 4.38(1H,dd,J=11.0, 9.4Hz), 4.67(1H,dd,J=11.0, 3.7Hz) |
| 12 | 582(M+2)$^+$ | 3410, 3340, 1720, 1690, 1670, 1625, 1545, 1515, 1455, 1330, 1065 | 1.97(3H,s), 2.09(1H,m), 2.31 (3H,s), 2.41(1H,dd of ABd, J= 17.4, 9.9, 6.0Hz), 2.45(1H,dd of ABd,J=17.4, 9.5, 6.3Hz), 2.55(1H,m), 2.60(1H,d,J=4.8 Hz) 2.70(1H,dd,J=4.8, 2.0Hz), 2.87(2H,t,J=6.3Hz), 3.00(2H,t, J=6.0Hz), 3.55(1H,t of AB,J= 14.0, 6.2Hz), 3.57(1H,t of ABd, J=14.0, 6.9Hz), 3.65(1H,dd,J= 13.6, 2.1Hz), 3.73(1H,dd,J= 9.4, 3.7Hz), 4.01(2H,br.t,J= 6.3Hz), 4.08(1H,d,J=13.6Hz), 4.31(1H,dd,J=8.9, 5.1Hz), 4.40(1H,dd,J=10.8, 9.5Hz), 4.69(1H,dd,J=10.9, 3.7Hz) |
| 13 | 568(M+2)$^+$ | 3435, 3280, 2950, 1720, 1700, 1680, 1630, 1560, 1510, 1460, 1440, 1325, 1200, 1120, 1060 | (Py-d$_5$) 1.64(2H,m), 2.00(3H,s) 2.03(2H,m), 2.74(1H,dd,J=4.4, 1.9Hz), 2.81(1H,m), 2.98(1H,m) 3.05(4H,m), 3.13(1H,d,J=4.4 Hz), 3.22(3H,s), 3.41(1H,m), 3.60(1H,dd,J=12.7, 1.9Hz), 3.77(1H,m), 3.90(1H,m), 3.98 (3H,m), 4.52(1H,d,J=12.7Hz), 5.04(1H,dd,J=11.0, 10.4Hz), 5.37(1H,dd,J=10.4, 4.2Hz), 7.27(1H,t,J=6.3Hz), 7.60(2H, br.) |

TABLE 7

| No. | IR(KBr)cm$^{-1}$ | $^1$H-NMR (CDCl$_3$) δ (400MHz) |
|---|---|---|
| 15 | 3300, 2930, 1705, 1655, 1635, 1565, 1510, 1440, 1320, 1260, 1200, 1055, 965, 855, 755 | 1.03(6H,s), 1.20~1.70(6H,m), 1.72(3H, s), 1.99(3H,s), 2.02(3H,s), 2.35(3H, s), 2.80~2.89(6H,m), 3.20( (3H,s), 3.51(1H,dd,J=12.8, 2.0Hz), 3.61(1H, dd,J=10.6, 4.4Hz), 3.64(2H,q,J=6.4Hz) 3.87(2H,q,J=5.9Hz), 4.27(1H,d,J=12.8 Hz), 4.50(1H,t,J=10.6Hz), 4.71(1H, dd,J=10.8, 4.4Hz), 4.78(1H,br.), 5.69 (1H,s), 6.04(1H,t,J=5.9Hz), 6.10~6.27 (4H,m), 6.52(1H,t,J=6.4Hz), 6.93(1H, dd,J=11.6, 15.0Hz) |
| 16 | 3280, 2925, 1720, 1710, 1670, 1650, 1560, 1520, 1460, 1325, 1220, 1140, 1060 | 0.84(3H,s), 0.85(3H,s), 0.87(6H,s), 1.01~1.57(21H,m), 1.57(3H,s), 1.77 (2H,m), 1.96(3H,s), 1.999(3H,s), 2.004(3H,s), 2.08(3H,s), 2.58(2H,t,J= 6.8Hz), 2.62(2H,t,J=6.8Hz), 2.80(2H, J=6.4Hz), 2.81(1H,br.), 2.86(2H,t,J= 6.4Hz), 2.87(1H,br.), 2.98(2H,t,J=6.8 Hz), 3.20(3H,s), 3.51(1H,br.d,J=12.9 Hz), 3.58(2H,q,J=6.3Hz), 3.60(1H,dd, J=10.1, 4.6Hz), 3.83(2H,q,J=6.3Hz), 4.27(1H,d,J=12.9Hz), 4.50(1H,br.t), 4.69(2H,br.), 4.71(1H,dd,J=10.7, 4.4 |

TABLE 8

| No. | SIMS (m/z) | IR(KBr)cm$^{-1}$ | $^1$H-NMR δ (400MHz) |
|---|---|---|---|
| 18 | 499(M+2)$^+$ 500(M+3)$^+$ | 3400, 2950, 1710, 1700, 1655, 1630, 1540, 1510, 1450, 1325, 1105, 1060, 800, 750 | (Py-d$_5$) 2.06(3H,s), 2.12(3H,s), 2.22 (1H,dd,J=4.9, 2.0Hz), 2.45(1H,d,J= 4.9Hz), 2.89(2H,t,J=6.6Hz), 2.99(2H, t,J=6.6Hz), 3.66(1H,dd,J=12.8, 2.0 Hz), 3.79(2H,q,J=6.6Hz), 3.83(2H,q, J=6.4Hz), 4.20(1H,dd,J=10.0, 3.4Hz), 4.42(1H,d,J=12.9Hz), 5.18(1H,t,J= 10.3Hz), 5.44(1H,dd,J=10.5, 3.4Hz), 7.20(1H,br.t), 7.44(2H,br.), 8.53 1H,d,J=1.2Hz), 8.98(1H,br.) |
| 19 | 567(M+2)$^+$ | 3300, 1720, 1705, 1635, 1560, 1515, 1450, 1325, 1210, 1155, 1060 | (CDCl$_3$) 0.61(1H,br.), 2.02(3H,s), 2.82(1H,br.), 2.852(1H,t of AB d,J= 13.9, 6.6Hz), 2.860(1H,t of AB d,J= 13.9, 6.6Hz), 2.90(1H,br.), 2.923 (1H,t of AB d,J=13.9, 6.4Hz), 2.927 (1H,t of AB d,J=13.9, 6.4Hz), 3.21 (3H,s), 3.52(1H,br.d,J=13.0Hz), 3.60(1H,dd,J=10.5, 4.4Hz), 3.73(2H, br.q,J=6.4Hz), 3.86(2H,q,J=6.3Hz), 4.27(1H,d,J=12.9Hz), 4.51(1H,br.t), 4.68(1H,dd,J=10.8, 4.4Hz), 4.70(2H, br.), 6.49(1H,t,J=6.2Hz), 7.16(1H, br.) |
| 20 | 567(M+2)$^+$ | 3360, 1715, 1705, 1645, 1550, 1530, 1450, 1330, 1210, 1185, 1155, 1065 | (CDCl$_3$) 2.00(3H,s), 2.25(1H,d,J= 4.7Hz), 2.27(3H,s), 2.28(1H,dd,J= 4.7, 1.8Hz), 2.824(1H,t of AB d,J= 14.0, 6.8Hz), 2.864(1H,t of AB d,J= 14.0, 6.8Hz), 2.92(1H,dd of AB d,J= 13.8, 6.3, 6.1Hz), 3.51(1H,dd,J= 13.0, 1.9Hz), 3.68(1H,dd,J=6.5, 2.3 Hz), 3.713(1H,q of AB d,J=13.0, 6.4 Hz), 3.739(1H,q of AB d,J=13.0, 6.4 Hz), 3.86(2H,q,J=6.2Hz), 4.17(1H,d, J=13.0Hz), 4.38(1H,s), 4.67(1H,dd, J=11.6, 2.3Hz), 4.73(2H,br.), 4.76 (1H,dd,J=11.6, 6.5Hz), 6.50(1H,t,J= 6.2Hz), 7.21(1H,br.) |

TABLE 7-continued

| No. | IR(KBr)cm$^{-1}$ | $^1$H-NMR (CDCl$_3$) δ (400MHz) |
|---|---|---|
| | | Hz), 6.26(1H,br.t,J=6.1Hz), 6.50(1H, br.t,J=6.2Hz) |

TABLE 9

| No. | SIMS (m/z) | IR (KBr) | $^1$H-NMR (D$_2$O) δ (400MHz) |
|---|---|---|---|
| 22 | 613(M+1)$^+$ 614(M+2)$^+$ | 3230, 2930, 1700, 1635, 1560, 1545, 1505, 1440, 1325, 1060 | 1.71(3H,m), 1.86(1H,m), 1.92*(s), 1.99(3H,s), 2.72(2H,m), 2.94~3.05 (6H,m), 3.06(1H,br.), 3.09(1H,d,J= 4.6Hz), 3.27(3H,s), 3.43*(dd), 4.30*(dd), 4.41*(dd), 3.62(1H,br. d,J=13.3Hz), 3.64(1H,dd,J=10.7, 4.7 Hz), 4.01(2H,t,J=6.3Hz), 4.17(1H,d, J=13.3Hz), 4.20(1H,m), 4.24(1H,t, J=10.7Hz), 4.58(1H,dd,J=10.7, 4.6Hz), |
| 23 | 627(M+1)$^+$ 628(M+2)$^+$ | 3280, 2860, 1705, 1630, 1555, 1510, 1450, 1395, 1320, 1060 | 1.42(2H,quintet,J=7.5Hz), 1.69(3H, m), 1.82(1H,m), 1.92*(s), 2.00(3H,s), 2.70(1H,t of ABd,J=15.1, 6.3Hz), 2.74(1H,t of ABd,J=15.1, 7.0Hz), 2.94~ 3.01(6H,m) 3.05(1H,br.), 3.09(1H,d, J=4.6Hz), 3.28(3H,s), 3.43*(s), 4.31* (dd), 4.41*(dd), 3.63(1H,br.d,J=12.9 Hz), 3.64(1H,dd,J=10.7, 4.6Hz), 4.01(2H, t,J=6.3Hz), 4.17(1H,d,J=12.9Hz), 4.19 (1H,dd,J=8.2, 5.0Hz), 4.25(1H,t,J= 10.7Hz), 4.31*(s), 4.41*(s), 4.59 (1H,dd,J=10.7, 4.6Hz) |
| 24 | 613(M+1)$^+$ 614(M+2)$^+$ 615(M+3)$^+$ | 3400, 3280, 1710, 1630, 1590, 1540, 1510, 1450, 1400, 1330 | 1.72(3H,m), 1.87(1H,m), 1.98(3H,s), 2.30(3H,s), 2.60(1H,d,J=4.8Hz), 2.70 (1H,dd,J=4.8, 2.0Hz), 2.73(2H,m), 2.96(2H,t,J=6.7Hz), 3.01(4H,m), 3.65(1H,dd,J=13.6, 2.0Hz), 3.72(1H, dd,J=9.3, 3.6Hz), 4.02(2H,t,J=6.3 Hz), 4.08(1H,d,J=13.6Hz), 4.21(1H, dd,J=7.5, 4.8Hz), 4.40(1H,dd,J= 10.8, 9.4Hz), 4.68(1H,dd,J=10.8, 3.6Hz) |
| 25 | 627(M+1)$^+$ 628(M+2)$^+$ 629(M+3)$^+$ | 3400, 3300, 1710, 1630, 1540, 1510, | 1.41(2H,quintet,J=7.8Hz), 1.68(3H,m) 1.83(1H,m), 1.98(3H,s), 2.30(3H,s), 2.60(1H,d,J=4.8Hz), 2.70(1H,dd,J= |

TABLE 9-continued

| No. | SIMS (m/z) | IR (KBr) | $^1$H-NMR (D$_2$O) δ (400MHz) |
|---|---|---|---|
| | | 1460, 1410, 1335 | 4.8, 1.9Hz), 2.72(2H,m), 2.94~3.03 (6H,m), 3.65(1H,dd,J=13.6, 1.9Hz), 3.72(1H,dd,J=9.2, 3.5Hz), 4.02(2H, t,J=6.3Hz), 4.08(1H,d,J=13.6Hz), 4.19(1H,dd,J=8.4, 5.0Hz), 4.40(1H, dd,J=10.8, 9.4Hz), 4.68(1H,dd,J= 10.9, 3.6Hz) |

TABLE 10

| No. | SIMS (m/z) | IR (KBr)cm$^{-1}$ | $^1$H-NMR (CDCl$_3$) δ (400MHz) (main peaks) |
|---|---|---|---|
| 27 | 859(M+3)$^+$ | 3285, 2920, 2870, 1720, 1630, 1555, 1510, 1450, 1315, 1255, 1210, 1055 | 0.85(3H, S), 2.03(3H, S), 2.76(2H, t, J=6.9Hz), 2.81(1H, br.s), 2.87(2H, t, J=6.6Hz), 2.96(2H, t, J=6.9Hz), 3.21 (3H, s), 3.51(1H, br.d, J=12.9Hz), 3.60(1H, dd, J=10.5, 4.3Hz), 3.88(2H, q, J=6.5Hz), 4.27(1H, d, J=12.9Hz), 4.50(1H, br.t, J=10.4Hz), 4.70(1H, dd, J=10.7, 4.3Hz), 4.74(1H, dd, J=8.9, 7.9Hz), 6.49(1H, t, J=6.1Hz), 6.92 (1H, br.d, J=2.5Hz), 6.97(1H, dd, J=6.4, 2.5Hz), 7.33 (1H, d, J=8.4Hz), 7.50(2H, t, J=7.7Hz), 7.63(1H, tt, J=7.4, 1.3Hz), 8.19(2H, dd, J=8.4, 1.3Hz) |
| 28 | 844(M+2)$^+$ | 3455, 2920, 1730, 1700, 1550, 1510, 1450, 1330, 1265, 1060 | 0.87(3H, s), 2.01(3H, s), 2.24(1H, d, J=4.7Hz), 2.26(3H, s), 2.27(1H, dd, J=4.7, 1.8Hz), 2.96(2H, t, J=6.5Hz), 3.51(2H, AB, J=14.7Hz), 3.51(1H, dd, J=12.9, 1.8Hz), 3.70 (1H, t, J=4.6Hz), 3.90(2H, q, J=6.3Hz), 4.15(1H, d, J=12.9 Hz), 4.51(1H, br.s), 4.71(2H, m), 4.76(1H, dd, J=9.0, 7.9Hz), 6.49(1H, t, J=6.3Hz), 6.81(1H, br.d, J=2.5Hz), 6.97(1H, dd, J=8.4, 2.5Hz), 7.33(1H, br.d, J=8.4Hz), 7.50 (2H, t, J=7.9Hz), 7.63(1H, tt, J=7.4, 1.3Hz), 8.19(1H, dd, J=8.4, 1.3Hz) |
| 29 (*)$^1$ | 585(M+2)$^+$ | 3280, 2930, 1740, 1735, 1720, 1715, 1710, 1680, 1635, 1545, 1520, 1465, 1320, 1200, 1065 | 1.11(3H, t, J=7.1Hz), 2.08(1H, br.s), 2.11(3H, s), 2.75 (1H, br.s), 2.91(2H, t, J=6.5Hz), 2.93(2H, t, J=6.9Hz), 3.13(1H, br.s), 3.22(3H, s), 3.22(2H, t, J=7.1Hz), 3.59 (1H, br.d, J=12.7Hz), 3.90(2H, q, J=6.8Hz), 3.98(1H, dd, J=11.2, 4.2Hz), 4.11(2H, q, J=7.1Hz), 4.32(2H, d, J= 5.9Hz), 4.52(1H, d, J=12.7Hz), 5.06(1H, t, J=10.6Hz), 5.36(1H, dd, J=10.4, 4.2Hz), 7.22(1H, t, J=6.3Hz), 7.60 (2H, br.s), 9.38(1H, t, J=5.9Hz) |
| 30 (*)$^2$ | 585(M+2)$^+$ 586(M+3)$^+$ | 3290, 2930, 1730, 1720, 1710, 1700, 1680, 1630, 1560, 1510, 1450, 1325, 1190, 1060 | 1.10(3H, t, J=7.1Hz), 1.65(3H, d, J=7.0Hz), 2.09(1H, br.s), 2.12(3H, s), 2.74(1H, br.s), 3.14(2H, m), 3.10 (1H, br.s), 3.21(3H, s), 3.58(1H, br.d, J=12.7Hz), 3.92, 3.93(1H, q, J=7.0Hz), 3.98(2H, q, J=6.6Hz), 4.00 (1H, br.), 4.14(2H, q, J=7.1Hz), 4.33(2H, d, J=5.8Hz), 4.51(1H, d, J=12.7Hz), 5.04(1H, t, J=10.8Hz), 5.35(1H, dd, J=10.2, 4.0Hz), 7.24(1H, br.t, J=5.9Hz), 7.60(2H, br.s), 9.57(1H, br.s) |
| 31 | 635(M+2)$^+$ | 3285, 2940, 1720, 1705, 1665, 1555, 1515, 1450, 1330, 1060 | 2.08(1H, br.), 2.11(3H, s), 2.75(1H, br.), 2.81(2H, t, J= 7.1Hz), 2.91(2H, t, J=6.8Hz), 2.92(2H, t, J=7.2Hz), 3.14 (1H, br.), 3.22(3H, s), 3.23(1H, t, J=7.1Hz), 3.59(1H, br.d, J=12.7Hz), 3.73(2H, q, J=6.7Hz), 3.90(2H, q, J= 6.7Hz), 3.98(1H, dd, J=11.1, 4.2Hz), 4.51(1H, d, J= 12.7Hz), 5.06(1H, dd, J=11.1, 10.4Hz), 5.36(1H, dd, J=10.4, 4.2Hz), 6.79(1H, dd, J=8.0, 2.0Hz), 7.17(1H, d, J=8.0Hz), 7.21(1H, d, J=2.0Hz), 7.23(1H, br.), 7.62(2H, br.), 8.67(1H, t, J=5.5Hz), 10.94(2H, br.) |
| 32 | 651(M+2)$^+$ 652(M+3)$^+$ | 3300, 1715, 1710, 1645, 1630, 1560, 1545, 1540, 1520, 1455, 1325, 1060 | 2.10(1H, br.), 2.11(3H, s), 2.75(1H, br), 2.88(2H, t, J= 7.2Hz), 2.92(1H, t, J=68Hz), 3.14(1H, br.), 3.22(3H, s) 3.23(1H, d, J=7.1Hz), 3.59(1H, br.d, J=12.7Hz), 3.87 (1H, m), 3.90(2H, q, J=6.7Hz), 3.98(1H, dd, J=11.1, 4.3 Hz), 4.06(1H, m), 4.52(1H, d, J=12.7Hz), 5.01(1H, dd, J=11.1, 10.4Hz), 5.28(1H, dd, J=7.9, 4.4Hz), 5.37 (1H, dd, J=10.4, 4.2Hz), 7.11(1H, br.), 7.17(1H, dd, J= 8.1, 2.0Hz), 7.25(1H, d, J=8.1Hz), 7.64(1H, d, J=2.0Hz) 7.64(2H, br.), 8.89(1H, t, J=5.7Hz), 11.04(2H, br.) |

TABLE 11

| No. | SIMS (m/z) | IR (MBr)cm$^{-1}$ | $^1$H-NMR (CDCl$_3$) δ (400MHz) |
|---|---|---|---|
| 34 | 530(M+2)$^+$ | 3350, 3280, 1720, 1715, 1700, 1695, 1690, 1625, 1560, 1545, 1540, 1525, 1455, 1320, 1110, 1055 | 2.01(3H, s), 2.24(1H, d, J=4.7Hz), 2.27(3H, s), 2.27(1H, dd, J=4.7, 1.9Hz), 2.35(3H, s), 2.83(2H, m), 2.88(2H, t, J=6.7Hz), 3.19(2H, m), 3.50(1H, dd, J=13.0, 2.0Hz) 3.70(1H, dd, J=5.4, 3.6Hz), 3.87(2H, q, J=6.5Hz), 4.16 (1H, d, J=13.0Hz), 4.38(1H, s), 4.72(2H, m), 4.72(2H, br.), 6.46(1H, br.t, J=6.5Hz), |
| 35 | Not found | 3440, 3290, 2930, 1710, 1635, 1565, 1505, 1450, 1325, 1240, 1145, 1060, 965, 855, 830, | 1.03(6H, s), 1.20~1.70(6H, m), 1.71(3H, s), 2.00(3H, s) 2.03(3H, s), 2.35(3H, s), 2.81(1H, br.), 2.88(2H, t, J= 6.6Hz), 2.96(1H, br.), 2.96(2H, t, J=6.6Hz), 3.20(3H, s) 3.51(1H, br.d, J=12.3Hz), 3.60(1H, dd, J=10.6, 4.4Hz) 3.88(2H, q, J=6.6Hz), 4.27(1H, d, J=13.0Hz), 4.37(2H, |

TABLE 11-continued

| No. | SIMS (m/z) | IR (MBr)cm$^{-1}$ | $^1$H-NMR (CDCl$_3$) δ (400MHz) |
|---|---|---|---|
| | | 760 | t, J=6.6Hz), 4.51(1H, br.t, J=10.8Hz), 4.69(1H, dd, J=10.8, 4.4Hz), 4.75(2H, br.), 5.77(1H, s), 6.12~6.31 (4H, m), 6.47(1H, t, J=6.2Hz), 7.02(1H, dd, J=14.8, 11.3 Hz). |

TABLE 12

| No. | SIMS (m/z) | IR (KBr)cm$^{-1}$ | $^1$H-NMR (Py-d$_5$) δ |
|---|---|---|---|
| 38 | 551(M+2)$^+$ | 3440, 3250, 3190, 1730, 1720, 1710, 1690, 1685, 1660, 1540, 1520, 1500, 1405, 1320, 1205, 1155, 1105, 1065, 990 | (100MHz)2.09(3H, s), 2.13(3H, s), 2.24(1H, dd, J=4.8, 1.7Hz), 2.48(1H, d, J=4.8Hz), 2.95(2H, t, J=6.6 Hz), 3.67(1H, dd, J=12.9, 1.7Hz), 3.89(2H, s), 3.91 (2H, q, J=6.6Hz), 4.22(1H, dd, J=9.5, 3.6Hz), 4.45(1H, d, J=12.9Hz), 5.20(1H, dd, J=10.5, 9.5Hz), 5.42(1H, dd, J=10.5, 3.6Hz), 7.25(1H, br.t, J=6.2Hz), 7.52(2H, br.), 7.82(1H, s) |
| 39 | 668(M+2)$^+$ | 3400, 3290, 1700, 1695, 1680, 1675, 1555, 1545, 1505, 1455, 1320, 1275, 1050 | (400MHz)2.12(4H, s), 2.73(3H, m), 3.01(2H, m), 3.15 (1H, br.), 3.23(3H, s), 3.60(1H, br.d, J=13.0Hz), 3.75 (1H, d, J=13.0Hz), 3.90(1H, d, J=13.0Hz), 3.95(2H, q, J=6.8Hz), 3.99(1H, dd, J=11.2, 4.2Hz), 4.15(1H, br. dd, J=11.8, 2.5Hz), 4.24(1H, br.dd, J=11.8, 2.5Hz), 4.49(1H, q, J=1.3Hz), 4.53(1H, d, J=12.7Hz), 5.07(2H, m) 5.38(1H, dd, J=10.3, 4.2Hz), 6.99(1H, br.), 7.01(1H, t, J=6.4Hz), 7.20(1H,br.), 7.25(1H, t, J=6.5Hz), 7.64(2H, br.), 8.63(1H, s) |
| 40 | 668(M+2)$^+$ 669(M+3)$^+$ | 3400, 1715, 1700, 1695, 1675, 1545, 1540, 1525, 1510, 1470, 1340, 1270, 1100, 1055 | (400MHz)2.08(3H, s), 2.13(3H, s), 2.24(1H, dd, J=4.7, 1.9Hz), 2.48(1H, d, J=4.7Hz), 2.74(2H, m), 2.94(2H, m), 3.67(1H, dd, J=12.9, 1.9Hz), 3.71(1H, d, J=13.0Hz), 3.88(1H, d, J=13.0Hz), 3.89(2H, q, J=6.0Hz), 4.16(1H, br.d, J=11.1Hz), 4.24(1H, br.d, J=11.1Hz), 4.24(1H, dd, J=10.0, 3.4Hz), 4.44(1H, d, J=12.9Hz), 4.49(1H, q, J=3.2Hz), 5.06(1H, br.), 5.22(1H, dd, J=10.3, 10.0Hz), 5.47(1H, dd, J=10.5, 3.4Hz), 6.99(1H, br.), 7.01(1H, t, J=6.4Hz), 7.20(1H, br.), 7.24(1H, t, J=6.4Hz), 7.53(2H, br.), 8.35(1H, br.), 8.61(1H, s) |

TABLE 13

| No. | SIMS (m/z) | IR(KBr)cm$^{-1}$ | $^1$H-NMR δ |
|---|---|---|---|
| d | 887(M+1)$^+$ | 3305, 1740, 1685, 1640, 1545, 1350, 1275, 1205, 1175 | (CDCl$_3$)(400MHz)1.84(2H, m), 1.99(2H, m), 2.18(4H, m), 2.67(4H, t, J=7.1Hz), 3.28(1H, q, J=6.4Hz), 4.36(2H, m), 5.08(4H, s), 5.13 (2H, d of AB, J=12.4Hz), 5.17(2H, d of AB, J=12.4Hz), 5.81(2H, br.d, J=7.2Hz), 6.20 (2H, br.), 7.325(10H, s), 7.333(10H, s) |
| e | 915(M+1)$^+$ | 3305, 2935, 1735, 1670, 1640, 1545, 1535, 1450, 1275, 1205, 1170, 1055, 725, 695 | (CDCl$_3$)(400MHz)1.60(4H, m), 2.16(8H, m), 2.64(4H, t, J=7.0Hz), 3.19(4H, q, J=6.0Hz), 4.32(2H, m), 5.08(4H, s), 5.14(4H, s), 5.90 (2H, br.d), 6.10(2H, br.), 7.34(20H, s) |
| f (2TFA salt) | 375(M+1)$^+$ | 3270, 1700, 1680, 1650, 1550, 1420, 1260 | (D$_2$O)(400MHz)2.11(2H, m), 2.45(4H, m), 2.55(2H, m), 2.90(4H, t, J=6.3Hz), 3.58(4H, t, J=6.3Hz), 4.33(2H, dd, J=9.0, 5.1Hz) |
| g | 545(M+1)$^+$ | 3310, 2980, 1685, 1665, 1540, 1425, 1365, 1235, 1160, 1120 | (CDCl$_3$)(90MHz)1.44(18H, s), 1.40~1.70 (8H, m), 2.80(4H, t), 3.44(4H, m), 3.58(4H, q), 4.26(2H, br.), 7.00(2H, br) |

Note: TFA ... Trifuluoroacetic acid

TABLE 14

| No. | SIMS (m/z) | IR(KBr)cm$^{-1}$ | $^1$H-NMR (CDCl$_3$) δ (400MHz) |
|---|---|---|---|
| h | 503(M+1)$^+$ | 3350, 2970, 1735, 1680, 1660, 1515, 1370, 1300, 1250, 1170, 1030, 1005, 735 | 1.46(9H, s), 2.48(2H, t, J=7Hz), 2.70(1H, dd, J=16.6Hz), 3.04(1H, dd, J=16.5Hz), 3.35 (2H, q, J=7Hz), 3.63(2H, s), 3.76(3H, s), 4.45(1H, m), 5.09(2H, s), 5.61(1H, br.d), 6.75(1H, br.), 6.79(2H, d, J=8Hz), 7.19(2H, d, J=8Hz), 7.31(5H, s) |
| i | 517(M+1)$^+$ | 3360, 3330, 2930, 1720, 1680, 1650, 1505, 1285, 1245, 1195, 805, 745, 670 | 1.41(9H, s), 2.00(2H, m), 2.50(4H, m), 3.35 (2H, q, J=7Hz), 3.62(2H, s), 3.74(3H, s), 4.09(1H, m), 5.10(2H, s), 5.20(1H, m), 6.42 (1H, br.s), 6.79(2H, d, J=8Hz), 7.17(2H, d, J=8Hz), 7.30(5H, s) |
| j | 551(M+1)$^+$ | 3295, 2950, | 2.07(2H, m), 2.50(4H, t, J=7Hz), 3.34(2H, q, |

TABLE 14-continued

| No. | SIMS (m/z) | IR(KBr)cm$^{-1}$ | $^1$H-NMR (CDCl$_3$) δ (400MHz) |
|---|---|---|---|
| | | 1730, 1690, 1645, 1535, 1510, 1255, 1170, 1050, 1030, 815, 745, 700 | J=7Hz), 3.62(2H, s), 3.75(3H, s), 4.24(1H, q, J=7Hz), 5.09(4H, s), 5.78(1H, d, J=7Hz), 6.75(1H, br.), 76.83(2H, d, J=9Hz), 7.22(2H, d, J=9Hz), 7.33(10H, s) |
| k | 551(M+1)$^+$ | 3310, 2930, 1730, 1695, 1635, 1540, 1515, 1275, 1240, 1205, 1185, 1170, 1065, 1030, 830, 755, 735, 700 | 2.17(4H, br.), 2.52(2H, t, J=6Hz), 3.34(2H, q, J=6Hz), 3.44(3H, s), 3.64(2H, s), 4.43 (1H, m), 5.10(2H, s), 5.16(2H, s), 5.67(1H, br.s), 5.93(1H, br.s), 6.82(2H, d, J=9Hz), 7.20(2H, d, J=9Hz), 7.33(10H, s) |

TABLE 15

| No. | SIMS (m/z) | IR(KBr)cm$^{-1}$ | $^1$H-NMR (CDCl$_3$) δ |
|---|---|---|---|
| o | 887(M+1)$^+$ | 3330, 2940, 1740, 1690, 1645, 1540, 1265 | (90MHz) 1.65(8H, m), 2.50~3.20(12H, m), 3.64(2H, m), 4.58(2H, br.), 5.03(4H, s), 5.12(4H, s), 5.42(2H, br.), 7.10(2H, br.), 7.30 (20H, s) |
| p | 915(M+1)$^+$ | 3330, 1730, 1690, 1645, 1540, 1260 | (100MHz) 1.30(8H, m), 1.75(4H, m), 2.51(4H, m), 2.85 (4H, m), 3.03(4H, m), 4.57(2H, m), 4.90(2H, br.), 5.03(4H, s), 5.10(4H, s), 6.60(2H, br.), 7.29(20H, s) |

TABLE 16

| No. | SIMS (m/z) | IR(KBr)cm$^{-1}$ | $^1$H-NMR (D$_2$O) δ (400Hz) |
|---|---|---|---|
| q | 439(M+1)$^+$ | 3200, 1630, 1600, 1560, 1400, 1260, 1160, 1030 | 1.77(6H, m), 1.92(2H, m), 2.76(4H, t, J=6.6 Hz), 2.98(2H, t of AB d, J=13.6, 6.7Hz), 3.01(2H, t of AB d, J=13.6, 6.7Hz), 3.04 (4H, t, J=6.8Hz), 4.31(2H, dd, J=7.9, 5.1Hz) |
| r | 467(M+1)$^+$ | 3450, 1650, 1580, 1400, 1260, 1165, 1030 | 1.44(4H, quintet, J=8.0Hz), 1.70(6H, m), 1.85(2H, m), 2.73(4H, t of AB d, J=15.1, 6.7 Hz), 2.76(4H, dd of AB d, J=15.2, 7.0, 6.4 Hz), 2.99(8H, m), 4.25(2H, dd, J=8.6, 5.0Hz) |

We claim:

1. The compound of the structural formula as follows:

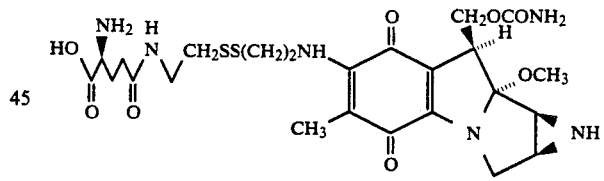

7-N-[2-[[2-(N$^5$-L-glutamino)ethyl]dithio]ethyl]-mitomycin C.

* * * * *